US012269805B2

(12) United States Patent
Holinstat et al.

(10) Patent No.: US 12,269,805 B2
(45) Date of Patent: *Apr. 8, 2025

(54) INHIBITORS OF PLATELET FUNCTION AND METHODS FOR USE OF THE SAME

(71) Applicants: THE REGENTS OF THE UNIVERSITY OF MICHIGAN, Ann Arbor, MI (US); THE REGENTS OF THE UNIVERSITY OF CALIFORNIA, Oakland, CA (US)

(72) Inventors: Michael Holinstat, Ann Arbor, MI (US); Reheman Adili, Ypsilanti, MI (US); Andrew White, Ann Arbor, MI (US); Theodore R. Holman, Santa Cruz, CA (US)

(73) Assignees: THE REGENTS OF THE UNIVERSITY OF MICHIGAN, Ann Arbor, MI (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/969,519

(22) Filed: Oct. 19, 2022

(65) Prior Publication Data
US 2023/0140210 A1 May 4, 2023

Related U.S. Application Data

(63) Continuation of application No. 17/047,422, filed as application No. PCT/US2019/027881 on Apr. 17, 2019, now Pat. No. 11,498,905.

(60) Provisional application No. 62/659,024, filed on Apr. 17, 2018.

(51) Int. Cl.
*C07D 249/12* (2006.01)
*A61P 7/02* (2006.01)
*C07D 403/12* (2006.01)

(52) U.S. Cl.
CPC .............. *C07D 249/12* (2013.01); *A61P 7/02* (2018.01); *C07D 403/12* (2013.01)

(58) Field of Classification Search
CPC .................................................. C07D 249/12
USPC .................................................... 514/255.05
See application file for complete search history.

(56) References Cited

FOREIGN PATENT DOCUMENTS

| CN | 102099340 A | 6/2011 |
|---|---|---|
| CN | 103702999 A | 4/2014 |
| CN | 107849026 A | 3/2018 |
| WO | WO-2009/143039 A2 | 11/2009 |
| WO | WO-2013/022814 A1 | 2/2013 |
| WO | WO-2017/019819 A1 | 2/2017 |
| WO | WO-2017/223447 A1 | 12/2017 |

OTHER PUBLICATIONS

Ahrens et al., Humanizing mouse thrombi, Nat. Biotechnol., 26(1):62-63 (2008).
Barsch-Haubold et al., Cytosolic phospholipase A2 is phosphorylated in collagen-and thrombin-stimulated human platelets independent of protein kinase C and mitogen-activated protein kinase, J. Biol. Chem., 270(43):25885-25892 (1995).
Berge et al., Pharmaceutical salts, J. Pharm. Sci., 66(1):1-19 (1977).
Bunting et al., Arterial walls generate from prostaglandin endoperoxides a substance (prostaglandin X) which relaxes strips of mesenteric and coeliac ateries and inhibits platelet aggregation, Prostaglandins, 12(6):897-913 (1976).
Bunting et al., Proceedings: Formation of prostaglandin endoperoxides and rabbit aorta contracting substance (RCS) by coupling two enzyme systems, Br. J. Pharmacol., 56(3):344P-345P (1976).
Capodanno et al., Meta-Analyses of Dual Antiplatelet Therapy Following Drug-Eluting Stent Implantation: Do Bleeding and Stent Thrombosis Weigh Similar on Mortality?, J. Am. Coll Cardiol., 66(14):1639-1640 (2015).
Chen et al., Addition of clopidogrel to aspirin in 45,852 patients with acute myocardial infarction: randomised placebo-controlled trial, Lancet, 366:1607-1621 (2005).
Diener et al., Aspirin and clopidogrel compared with clopidogrel alone after recent ischaemic stroke or transient ischaemic attack in high-risk patients (MATCH): randomised, double-blind, placebo-controlled trial, Lancet, 364:331-337 (2004).
Falardeau et al., Metabolism of 8, 11, 14-eicosatrienoic acid in human platelets, Biochim Biophys Acta., 441(2):193-200 (1976).
Farrow et al., Proceedings: Thrombolytic and anti-thrombotic properties of dihomo-gamma-linolenate in vitro, Br. J. Pharmacol., 55(2):316P-317P (1975).
International Application No. PCT/US19/27881, International Preliminary Report on Patentability, mailed Oct. 29, 2020.
International Application No. PCT/US19/27881, International Search Report and Written Opinion, mailed Jul. 17, 2019.
Kernoff et al., Antithrombotic potential of dihomo-gamma-linolenic acid in man, Br. Med. J., 2:1441-1444 (1977).
Lands et al., Phospholipid precursors of prostaglandins, Biochim. Biophys Acta., 164(2):426-429 (1968).

(Continued)

*Primary Examiner* — Taofiq A Solola
(74) *Attorney, Agent, or Firm* — MARSHALL, GERSTEIN & BORUN LLP

(57) ABSTRACT

Disclosed herein are small molecule inhibitors of platelet function, and methods of using the small molecules to treat diseases, such as platelet hemostasis and thrombosis. In particular, disclosed herein are compounds of Formula (I) and pharmaceutically acceptable salts thereof: wherein the substituents are as described.

20 Claims, 7 Drawing Sheets

(56) References Cited

OTHER PUBLICATIONS

Lee et al., Safety and efficacy of targeting platelet proteinase-activated receptors in combination with existing anti-platelet drugs as antithrombotics in mice, Br. J. Pharmacol., 166(7):2188-2197 (2012).
Moncada et al., An enzyme isolated from arteries transforms prostaglandin endoperoxides to an unstable substance that inhibits platelet aggregation, Nature, 263:663-665 (1976).
Needleman et al., Manipulation of platelet aggregation by prostaglandins and their fatty acid precursors: pharmacological basis for a therapeutic approach, *Prostaglandins*, 19(1):165-181 (1980).
Palacio et al., Effect of Addition of Clopidogrel to Aspirin on Mortality: Systematic Review of Randomized Trials, *Stroke*, 43(8):2157-2162 (2012).
Srivastava, Metabolism of arachidonic acid by platelets: utilization of arachidonic acid by human platelets in presence of linoleic and dihomo-gamma-linolenic acids, Z. Emahrungswiss, 17(4):248-261 (1978).
Wada et al., Enzymes and Receptors of Prostaglandin Pathways with Arachidonic Acid-derived Versus Eicosapentaenoic Acid-derived Substrates and Products, *J Biol Chem*, 282(31):22254-22266 (2007).
Willis et al., Dihomo-gamma-linolenate suppresses platelet aggregation when administered in vitro or in vivo, Prostaglandins, 8(6):509-519 (1974).

INHIBITORS OF PLATELET FUNCTION AND METHODS FOR USE OF THE SAME

CROSS REFERENCE TO RELATED APPLICATION

This application claims priority to U.S. Provisional Patent Application No. 62/659,024, filed Apr. 17, 2018, the disclosure of which is hereby incorporated by reference in its entirety.

STATEMENT OF GOVERNMENT INTEREST

This invention was made with government support under GM105671 awarded by the National Institutes of Health. The government has certain rights in the invention.

BACKGROUND

Technical Field

The present disclosure relates to inhibitors of platelet function, and methods of using the inhibitors to treat diseases, such as platelet hemostasis and thrombosis.

Description of Related Technology

Platelet activation plays a critical role in the thrombotic complications associated with life-threatening cardiovascular ischemic events, such as myocardial infarction and stroke. Inhibiting platelet activation in individuals at risk for thrombotic events through the use of aspirin and $P2Y_{12}$ receptor antagonists has significantly decreased morbidity and mortality associated with these debilitating conditions (Chen et al., *Lancet* 366:1607-1621, 2005; Palacio et al., *Stroke* 43:2157-2162, 2012).

Polyunsaturated fatty acids ("PUFAs") as a dietary supplement have traditionally been used for their potential cardioprotective effects, including their antiplatelet effects. Dihomo-γ-linolenic acid ("DGLA"), an ω-6 PUFA, has been shown to inhibit platelet aggregation ex vivo (Farrow and Willis, *Br J Pharmacol* 55:316P-317P, 1975; Kernoff et al., *Br Med J* 2:1441-1444, 1977; Willis et al., *Prostaglandins* 8:509-519, 1974). In addition, platelets isolated from humans, as well as baboons, rabbits, and rats that received daily oral doses of DGLA had a significant reduction in ex vivo aggregation. PUFAs are primarily thought to exert their regulatory effects on platelet function through their conversion into bioactive lipids (oxylipins) by oxygenases (Wada et al., *J Biol Chem* 282:22254-22266, 2007). In platelets, DGLA can be oxidized by cyclooxygenase-1 ("COX-1") or platelet 12-lipoxygenase ("12-LOX") (Falardeau et al., *Biochim Biophys Acta* 441:193-200, 1976) following its release from the phospholipid bilayer predominately through the actions of cytoplasmic phospholipase $A_2$ (Borsch-Haubold et al., *The Journal of biological chemistry* 270:25885-25892, 1995; Lands and Samuelsson, *Biochim Biophys Acta* 164:426-429, 1968). While both COX-1 and 12-LOX are able to oxidize DGLA to their respective metabolites, the relative contributions of these oxylipid products to the inhibitory effects of DGLA on platelet function remain unclear. Historically, the antiplatelet effects of DGLA have been attributed solely to COX-1-derived metabolites that have been shown to inhibit platelet activation (Farrow and Willis, supra; Kernoff et al., supra; Srivastava, *Z Ernahrungswiss* 17:248-261, 1978; Willis et al., supra). However, the DGLA derived products of COX-1 ($TXA_1$ and $PGE_1$) are labile and produced in low amounts in platelets (Bunting et al., *Prostaglandins* 12:897-913, 1976a; Bunting et al., *Br J Pharmacol* 56:344P-345P, 1976b; Moncada et al., *Nature* 263:663-665, 1976; Needleman et al., *Prostaglandins* 19:165-181, 1980). Recently, 12(S)-hydroxyeicosatetrienoic acid ("12-HETrE"), the 12-LOX-derived oxylipin of DGLA, was found to exhibit a potential antiplatelet effect ex vivo. It was subsequently found that ω-6 PUFA, DGLA, inhibited platelet thrombus formation in vivo following an insult to the vessel wall. Interestingly, DGLA was unable to inhibit thrombus formation in $12\text{-}LOX^{-/-}$ mice suggesting the antithrombotic effects of DGLA were mediated by 12-LOX. The 12-LOX-derived oxylipin of DGLA, 12-HETrE, potently impaired thrombus formation following vessel injury irrespective of 12-LOX expression. Furthermore, the antiplatelet effect of 12-HETrE was shown to inhibit platelet function through activation of the $G\alpha_s$ signaling pathway leading to formation of cAMP and PKA activation in the platelet.

Advances in antiplatelet therapy have significantly decreased the risk for morbidity and mortality due to thrombosis. However, even with the current standard-of-care antiplatelet therapies available, myocardial infarction and stroke due to occlusive thrombotic events remains one of the primary causes of morbidity and mortality globally. The fact that the rate of ischemic events still remains high in individuals on antiplatelet agents (see Diener et al., *Lancet* 364:331-337, 2004) stresses the unmet clinical need for alternative therapies that reduce occlusive thrombotic events without promoting an increased risk of bleeding. Additionally, while traditional anti-platelet therapy has been useful for limiting platelet activation, its utility in disorders involving immune-targeting of the immune receptors on the platelet, such as immune thrombocytopenia ("ITP"), has been limited due to its propensity to cause bleeding and limited ability to prevent or inhibit platelet clearance. For these reasons, thrombotic disorders leading to platelet clearance, thrombosis, and bleeding remain a challenge to treat therapeutically.

SUMMARY

In one aspect, provided herein are compounds of Formula (I), or pharmaceutically acceptable salts thereof:

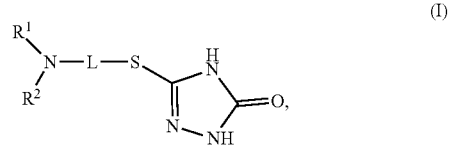

wherein: (a) each of $R^1$ and $R^2$ independently is $C_{6-10}$aryl optionally substituted with 1-2 groups selected from $C_{1-6}$alkyl, halo, and aryl; or (b) $R^1$ is HET and $R^2$ is $C_{1-6}$alkyl; HET is a heteroaryl group containing 1, 2, or 3 nitrogen atoms and 5 or 6 total ring atoms and optionally substituted with 1-2 groups selected from $C_{1-6}$alkyl, halo, and aryl; L is $-(CO_2)_s-(CH_2)_m-(Cy)_r-(CH_2)_n-$; Cy is $C_{3-8}$cycloalkylene; m is 1 or 2; n is 1, 2, 3, 4, or 5; and r and s are each independently 0 or 1.

In some embodiments, $R^1$ is HET and $R^2$ is $C_{1-6}$alkyl. In various embodiments, HET comprises pyrrolyl, pyrazolyl, imidazolyl, triazolyl, tetrazolyl, pyridinyl, pyridazinyl, pyrimidinyl, pyrazinyl, or triazinyl. In some cases, HET comprises pyrazinyl. In various cases, HET is substituted with one or two substituents. In some embodiments, HET is substituted with one substituent. In various embodiments, HET is substituted with two substituents. In some cases, HET is substituted one or two aryl groups. In various cases, aryl comprises phenyl. In various embodiments, $R^2$ is methyl, ethyl, propyl, isopropyl, butyl, s-butyl, t-butyl, isobutyl, pentyl, or hexyl. In some cases, $R^2$ is methyl, ethyl, propyl, or isopropyl. In various embodiments, $R^2$ is isopropyl. In some embodiments, HET is

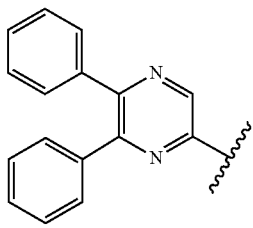 [SMILES: *c1cnc(-c2ccccc2)c(-c2ccccc2)n1]

and $R^2$ is isopropyl.

In some embodiments, each of $R^1$ and $R^2$ independently is $C_{6-10}$aryl. In various embodiments, $R^1$ and $R^2$ each comprise phenyl. In some cases, each phenyl is unsubstituted. In various cases, at least one phenyl is substituted with halo. In some cases, halo is Cl or F. In various cases, halo is Cl. In some embodiments, one of $R^1$ and $R^2$ is phenyl and the other of $R^1$ and $R^2$ is 4-chlorophenyl.

In some cases, r and s are each 1. In various cases, Cy comprises cyclobutylene, cyclopentylene, or cyclohexylene. In some embodiments, Cy comprises cyclopentylene or cyclohexylene. In various embodiments, Cy comprises cyclohexylene. In some cases, m is 1. In various cases, n is 1 or 2. In some embodiments, n is 1. In various embodiments, n is 2.

In some cases, r and s are each 0. In various cases, n+m is 3, 4, 5, or 6. In some embodiments, n+m is 3. In various embodiments, n+m is 4. In some cases, n+m is 5. In various cases, n+m is 6.

Specifically contemplated compounds of the disclosure include a compound selected from the group consisting of:

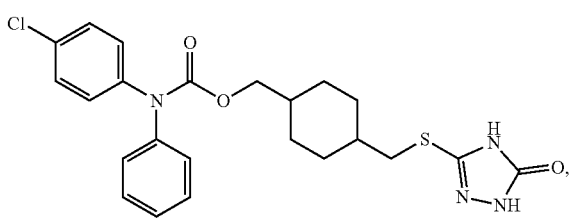

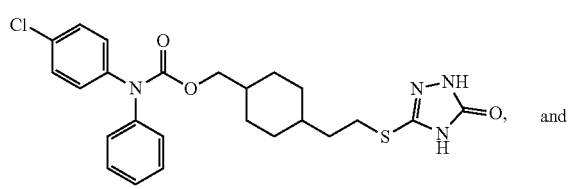

and

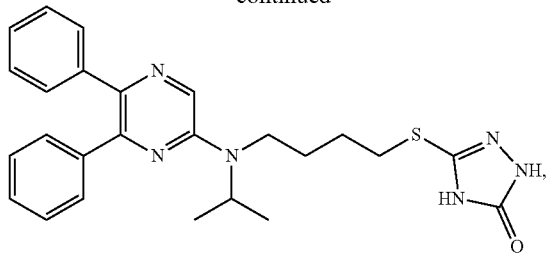

or a pharmaceutically acceptable salt thereof. In some cases, the disclosure provides compound A1, or a pharmaceutically acceptable salt thereof:

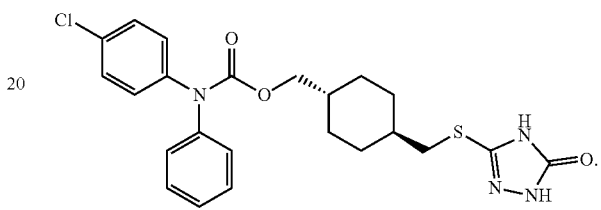

In various cases, the disclosure provides compound A2, or a pharmaceutically acceptable salt thereof:

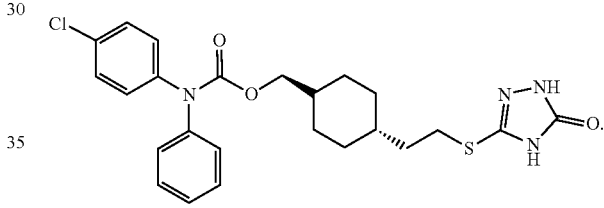

In some embodiments, the disclosure provides compound A3, or a pharmaceutically acceptable salt thereof:

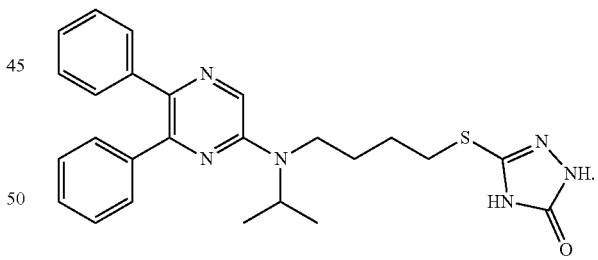

Also provided herein is a pharmaceutical composition comprising a compound or salt thereof described herein and a pharmaceutically acceptable carrier.

Further provided herein is a method of inhibiting platelet aggregation in a cell, comprising contacting the cell with a compound or composition described herein in an amount effective to inhibit platelet aggregation.

Also provided herein is a method of inhibiting platelet integrin activation in a cell, comprising contacting the cell with a compound or composition described herein in an amount effective to inhibit platelet integrin activation. In some embodiments, Rap1 activation is inhibited.

Further provided herein is a method of activating one or more of $G\alpha_s$-linked G Protein-coupled receptors ("GPCRs"), cAMP, and protein kinase A ("PKA") in a cell, comprising contacting the cell with a compound or composition described herein in an amount effective to activate GPCRs, cAMP and/or PKA.

Also provided herein is a method of inhibiting thrombus growth in a subject in need thereof, comprising administering to the subject a therapeutically effective amount of a compound or composition described herein.

Another aspect of the disclosure relates to a method of treating a thrombotic disorder in a subject in need thereof comprising administering to the subject a therapeutically effective amount of a compound or composition described herein. In some embodiments, the thrombotic disorder is selected from arterial thrombosis, deep vein thrombosis ("DVT"), pulmonary embolism ("PE"), ischemic stroke, immune thrombocytopenia ("ITP"), Heparin-induced thrombocytopenia ("HIT"), and Heparin-induced thrombocytopenia and thrombosis ("HITT").

Further provided herein is a method of preventing thrombosis in a subject comprising administering to the subject a therapeutically effective amount of a compound or composition described herein.

Also provided herein is method of treating thrombocytopenia in a subject in need thereof comprising administering to the subject a therapeutically effective amount of a compound or composition described herein.

Further aspects and advantages will be apparent to those of ordinary skill in the art from a review of the following detailed description, taken in conjunction with the drawings. The description hereafter includes specific embodiments with the understanding that the disclosure is illustrative, and is not intended to limit the invention to the specific embodiments described herein.

DETAILED DESCRIPTION

Figure 1:
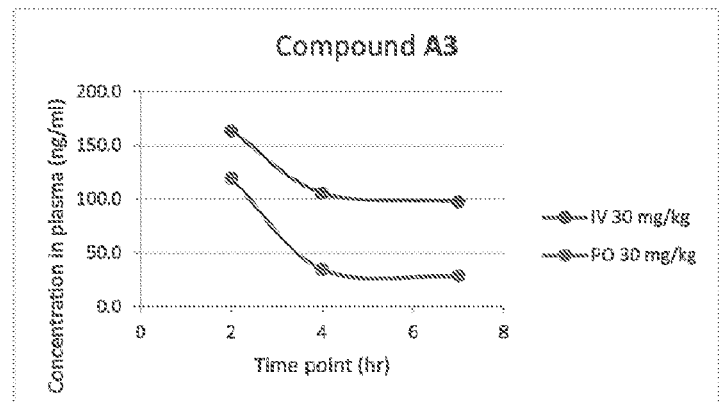
FIG. 1 depicts the concentration of oral- or IV-administered compound A3 (30 mg/kg) in the plasma of mice (n=3), monitored at 3 time points (2 h, 4 h, and 7 h), as further described in the Examples section.

Disclosed herein are compounds having a structure of Formula (I), or a pharmaceutically acceptable salt thereof:

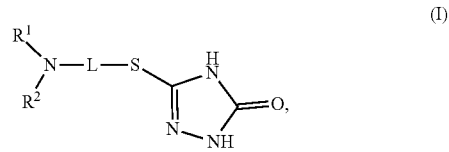

(I)

which have antiplatelet activity and are useful for treating thrombotic disorders, e.g., by preventing or inhibiting thrombosis, thrombocytopenia, and/or ischemia, without disrupting hemostasis. The compounds and methods of the present disclosure impair thrombus formation in vivo, providing cardioprotective effects through the attenuation of platelet function. Unlike other antiplatelet agents that cause excessive bleeding (Ahrens and Peter, *Nat Biotechnol* 26:62-63, 2008; Capodanno et al., *J Am Coll Cardiol* 66:1639-1640, 2015; Lee et al., *Br J Pharmacol* 166:2188-2197, 2012), the compounds and methods of the present disclosure do not significantly alter hemostasis and instead exert an anti-thrombotic effect, while at the same time maintaining primary hemostasis.

The compounds described herein are superior to 12(S)-hydroxyeicosatrienoic acid ("12(S)-HETrE"), which also has antiplatelet activity, in that they can inhibit platelet function in the single nanomolar range, can fully inhibit agonist-induced aggregation, and can induce vasodilator-stimulated phosphoprotein-phosphorylation ("VASP-phosphorylation") following addition of the compounds to human platelets at concentrations as low as 10 nM. Furthermore, the compounds described herein do not induce bleeding, can be administered orally or intravenously, and are stable in blood.

Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$ alkyl refers to an alkyl group having a number of carbon atoms encompassing the entire range (e.g., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "cycloalkyl" refers to a monovalent aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_{5-8}$ cycloalkyl refers to cycloalkyl groups having a number of carbon atoms encompassing the entire range (e.g., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated or fused to another cycloalkyl group, a heterocycloalkyl group, an aryl group and/or a heteroaryl group. When a cycloalkyl group is fused to another cycloalkyl group, then each of the cycloalkyl groups can contain three to eight carbon atoms. Cycloalkyl groups can be optionally substituted with, for example, one to three groups, independently selected alkyl, alkylene-OH, C(O)$NH_2$, $NH_2$, oxo (=O), aryl, haloalkyl, halo, and OH.

As used herein, the term "cycloalkylene" refers to a bivalent cycloalkyl group. For example, the term "cycloalkylene-aryl" refers to an cyclalkylene group substituted with an aryl group. The term $C_n$ means the cycloalkylene group has "n" carbon atoms. For example, $C_{3-6}$cycloalkylene refers to a cycloalkylene group having a number of carbon atoms encompassing the entire range, as well as all subgroups, as previously described for "cycloalkyl" groups.

As used herein, the term "aryl" refers to a cyclic aromatic group, such as a monocyclic aromatic group, e.g., phenyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Aryl groups can be isolated (e.g., phenyl) or fused to another aryl group (e.g., naphthyl, anthracenyl), a cycloalkyl group (e.g. tetrahydronaphthyl), a heterocycloalkyl group, and/or a heteroaryl group. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a cyclic aromatic ring having five to twelve total ring atoms (e.g., a monocyclic aromatic ring with 5-6 total ring atoms), and containing one to three heteroatoms selected from nitrogen, oxygen, and sulfur atom in the aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. In some cases, the heteroaryl group is substituted with one or more of alkyl and alkoxy groups. Heteroaryl groups can be isolated (e.g., pyridyl) or fused to another heteroaryl group (e.g., purinyl), a cycloalkyl group (e.g., tetrahydroquinolinyl), a heterocycloalkyl group (e.g., dihydronaphthyridinyl), and/or an aryl group (e.g., benzothiazolyl and quinolyl). Examples of heteroaryl groups include, but are not limited to, thienyl, furyl, pyridyl, pyrrolyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. When a heteroaryl group is fused to another heteroaryl group, then each ring can contain five or six total ring atoms and one to three heteroatoms in its aromatic ring.

As used herein, the term "halo" refers to a fluoro, chloro, bromo, or iodo group.

A used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

As used herein, the term "therapeutically effective amount" means an amount of a compound or combination of therapeutically active compounds that ameliorates, attenuates or eliminates one or more symptoms of a particular disease or condition, or prevents or delays the onset of one of more symptoms of a particular disease or condition.

As used herein, the terms "patient" and "subject" may be used interchangeably and mean animals, such as dogs, cats, cows, horses, and sheep (e.g., non-human animals) and humans. Particular patients or subjects are mammals (e.g., humans). The terms patient and subject includes males and females.

As used herein the terms "treating", "treat" or "treatment" and the like include preventative (e.g., prophylactic) and palliative treatment. In some cases, the treating refers to treating a symptom of a disorder or disease as disclosed herein.

Compounds

Provided herein are compounds of Formula (I), or pharmaceutically acceptable salts thereof:

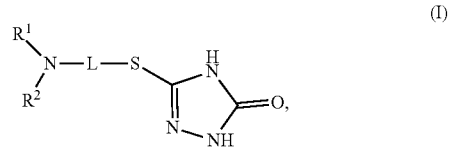

wherein:
(a) each of $R^1$ and $R^2$ independently is $C_{6-10}$aryl optionally substituted with 1-2 groups selected from $C_{1-6}$alkyl, halo, and aryl; or
(b) $R^1$ is HET and $R^2$ is $C_{1-6}$alkyl;
HET is a heteroaryl group containing 1, 2, or 3 nitrogen atoms and 5 or 6 total ring atoms and optionally substituted with 1-2 groups selected from $C_{1-6}$alkyl, halo, and aryl;
L is —(CO$_2$)$_s$—(CH$_2$)$_m$-(Cy)$_r$-(CH$_2$)$_n$—;
Cy is $C_{3-8}$cycloalkylene;
m is 1 or 2;
n is 1, 2, 3, 4, or 5; and
each of r and s independently is 0 or 1.

In some embodiments, $R^1$ is HET and $R^2$ is $C_{1-6}$alkyl. In various embodiments, HET comprises pyrrolyl, pyrazolyl, imidazolyl, triazolyl, tetrazolyl, pyridinyl, pyridazinyl, pyrimidinyl, pyrazinyl, or triazinyl. In some cases, HET comprises pyrazinyl. In various cases, HET is substituted with one or two substituents. In some embodiments, HET is substituted with one substituent. In various embodiments, HET is substituted with two substituents. In some cases, HET is substituted one or two aryl groups. In various cases, aryl comprises phenyl. In various embodiments, $R^2$ is methyl, ethyl, propyl, isopropyl, butyl, s-butyl, t-butyl, isobutyl, pentyl, or hexyl. In some cases, $R^2$ is methyl, ethyl, propyl, or isopropyl. In various embodiments, $R^2$ is isopropyl. In some embodiments, HET is

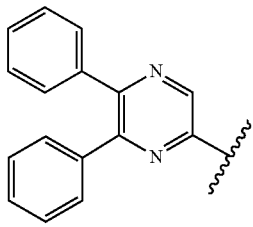 [SMILES: *c1cnc(-c2ccccc2)c(-c2ccccc2)n1]

and $R^2$ is isopropyl.

In some embodiments, each of $R^1$ and $R^2$ independently is $C_{6-10}$aryl. In various embodiments, $R^1$ and $R^2$ each comprise phenyl. In some cases, each phenyl is unsubstituted. In various cases, at least one phenyl is substituted with halo. In some cases, halo is Cl or F. In various cases, halo is Cl. In some embodiments, one of $R^1$ and $R^2$ is phenyl and the other of $R^1$ and $R^2$ is 4-chlorophenyl.

In some cases, r and s are each 1. In various cases, Cy comprises cyclobutylene, cyclopentylene, or cyclohexylene. In some embodiments, Cy comprises cyclopentylene or cyclohexylene. In various embodiments, Cy comprises cyclohexylene. In some cases, m is 1. In various cases, n is 1 or 2. In some embodiments, n is 1. In various embodiments, n is 2.

In some cases, r and s are each 0. In various cases, n+m is 3, 4, 5, or 6. In some embodiments, n+m is 3. In various embodiments, n+m is 4. In some cases, n+m is 5. In various cases, n+m is 6.

Specifically contemplated compounds of the disclosure include a compound selected from the group consisting of:

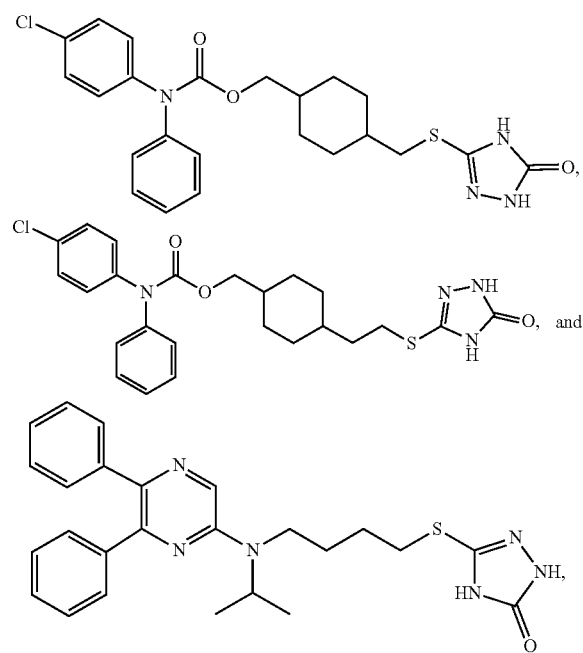

or a pharmaceutically acceptable salt thereof. In some cases, the disclosure provides compound A1 (CCG-263451), or a pharmaceutically acceptable salt thereof:

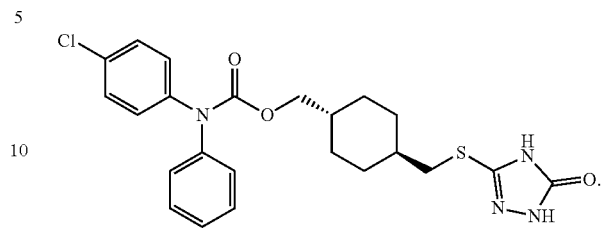

In various cases, the disclosure provides compound A2 (CCG-264085), or a pharmaceutically acceptable salt thereof:

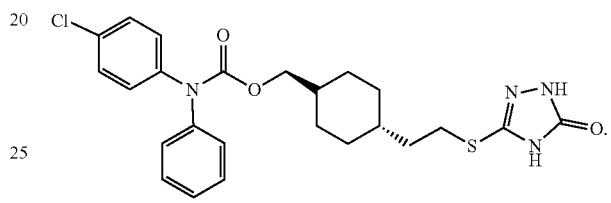

In some embodiments, the disclosure provides compound A3 (CCG-263720), or a pharmaceutically acceptable salt thereof:

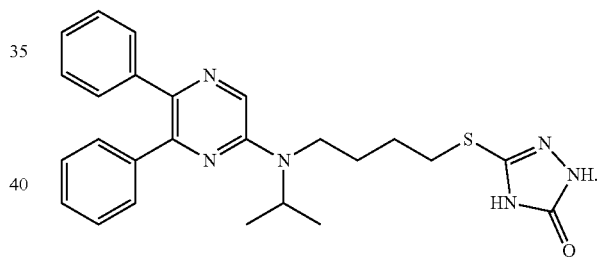

Compound Synthesis

The compounds provided herein can be synthesized using conventional techniques and readily available starting materials known to those skilled in the art. In general, the compounds provided herein are conveniently obtained via standard organic chemistry synthesis methods.

For example, either phenyl boronic acid or iodobenzene can be reacted with 4-chloroaniline to form 4-chloro-N-phenylaniline. The amino group can be reacted with triphosgene to form a carbonic acid group, which can be reacted with an appropriate (cyclohexane-14-diyl)dimethanol group to form a desired 4-(hydroxymethyl)cyclohexyl)methyl (4-chlorophenyl)(phenyl)carbamate compound. The carbamate compound can be alcohol-protected and reacted with 5-mercapto-2,4-dihydro-3H-1,2,4-triazol-3-one to form the desired compound. Alternatively, the carbamate compound can be oxidized to form an aldehyde and allowed to undergo a Wittig reaction to form the alkene. The alkene can be reacted with a boron reagent to form an alcohol, which can be protected and reacted with 5-mercapto-2,4-dihydro-3H-1,2,4-triazol-3-one to form the desired compound.

As another example, an appropriate ketone (e.g., propanone) can be reacted with 4-aminobutanol to form a desired 4-(amino)butan-1-ol, which can be reacted with 5-bromo-2,3-diphenylpyrazine to form a desired 4-((5,6-diphenylpyrazin-2-yl)amino)butan-1-ol compound. The chloro group can then be reacted with 5-mercapto-2,4-dihydro-3H-1,2,4-triazol-3-one to form the desired compound.

Additional synthetic procedures for preparing the inhibitors disclosed herein can be found in the Examples section.

Methods of Use

Adequate platelet reactivity is required for maintaining hemostasis. However, excessive platelet reactivity can also lead to the formation of occlusive thrombi. It has been found that the compounds described herein (e.g., the compounds of Formula (I), compounds A1, A2, and A3, and pharmaceutically acceptable salts of the foregoing) are able to inhibit platelet aggregation, which has implications for thrombosis and hemostasis. Thus, provided herein is a method of inhibiting platelet aggregation in a cell, comprising contacting the cell with a compound disclosed herein (e.g., a compound of Formula (I), compound A1, A2, or A3, or pharmaceutically acceptable salts of the foregoing), in an amount effective to inhibit platelet aggregation. In some embodiments, the contacting in in vivo. In various embodiments, the contacting is in vitro.

The compounds disclosed herein can inhibit platelet aggregation by impinging on intracellular signaling, specifically by inhibiting the activation of Rap1, a common signaling effector required for integrin $\alpha_{IIb}\beta_3$ activation. Without intending to be bound by theory, the antiplatelet effects of the compounds disclosed herein are believed to be mediated through the activation of the $G\alpha_s$ signaling pathway leading to formation of cAMP and PKA activation in the platelet. Thus, provided herein is a method of inhibiting integrin activation in a cell, comprising contacting the cell with a compound disclosed herein (e.g., a compound of Formula (I), compound A1, A2, or A3, or pharmaceutically acceptable salts of the foregoing), in an amount effective to inhibit integrin activation. Also provided herein is a method of inhibiting Rap1 activation in a cell, comprising contacting the cell with a compound disclosed herein (e.g., a compound of Formula (I), compound A1, A2, or A3, or pharmaceutically acceptable salts of the foregoing), in an amount effective to inhibit Rap1 activation. Further provided herein are methods of activating one or more of $G\alpha_s$-linked G Protein-coupled receptors ("GPCRs"), cAMP, and protein kinase A ("PKA") in a cell, comprising contacting the cell with a compound disclosed herein (e.g., a compound of Formula (I), compound A1, A2, or A3, or pharmaceutically acceptable salts of the foregoing) in an amount effective to activate GPCRs, cAMP and/or PKA. In some embodiments, the contacting in in vivo. In various embodiments, the contacting is in vitro.

Also provided herein is administration of a therapeutically effective amount of a compound disclosed herein (e.g., a compound of Formula (I), compound A1, A2, or A3, or pharmaceutically acceptable salts of the foregoing) to subject in need thereof. The ability of the compounds disclosed herein to inhibit platelet activation, thrombocytopenia, and/or thrombus formation in a subject in need thereof provides therapeutic efficacy in treating a wide range of thrombotic disorders. Particularly contemplated thrombotic disorders that can be treated or prevented via administration of a compound disclosed herein include arterial thrombosis, deep vein thrombosis ("DVT"), pulmonary embolism ("PE"), ischemic stroke, immune thrombocytopenia ("ITP"), Heparin-induced thrombocytopenia ("HIT"), and Heparin-induced thrombocytopenia and thrombosis ("HITT").

Further provided herein are methods of inhibiting thrombus growth, preventing thrombosis, and/or treating thrombocytopenia in a subject comprising administering to the subject a therapeutically effective amount of a compound disclosed herein (e.g., a compound of Formula (I), compound A1, A2, or A3, or pharmaceutically acceptable salts of the foregoing), in an amount effect to inhibit thrombus growth, prevent thrombosis, and/or treat thrombocytopenia in the subject.

Further guidance for using compounds disclosed herein having antiplatelet activity, such as a compound of Formula (I), compounds A1, A2, or A3, or pharmaceutically acceptable salts of the foregoing, can be found in the Examples section, below.

Pharmaceutical Formulations, Dosing, and Routes of Administration

The methods provided herein include the manufacture and/or use of pharmaceutical compositions, which include one or more of the compounds provided herein. Also included are the pharmaceutical compositions themselves. Pharmaceutical compositions typically include a pharmaceutically acceptable carrier. Thus, provided herein are pharmaceutical formulations that include a compound described herein (e.g., a compound of Formula (I), compound A1, A2, or A3, or a pharmaceutically acceptable salt of the foregoing), as previously described herein, and one or more pharmaceutically acceptable carriers.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Actual dosage levels of the active ingredients in the pharmaceutical compositions provided herein may be varied so as to obtain "therapeutically effective amount," which is an amount of the active ingredient effective to achieve the desired therapeutic response for a particular patient, composition, and mode of administration, without being toxic to the patient.

The concentration of a compound provided herein in a pharmaceutically acceptable mixture will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Other Embodiments

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims.

EXAMPLES

The following examples are provided for illustration and are not intended to limit the scope of the invention.

Synthesis of ((1r,4r)-4-(((5-oxo-4,5-dihydro-1H-1,2,4-triazol-3-yl)thio)methyl)cyclohexyl)methyl (4-chlorophenyl)(phenyl)carbamate (A1)

Scheme 1.

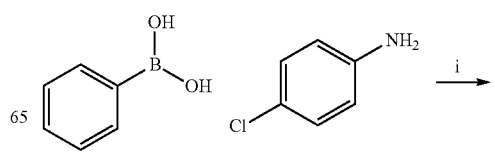

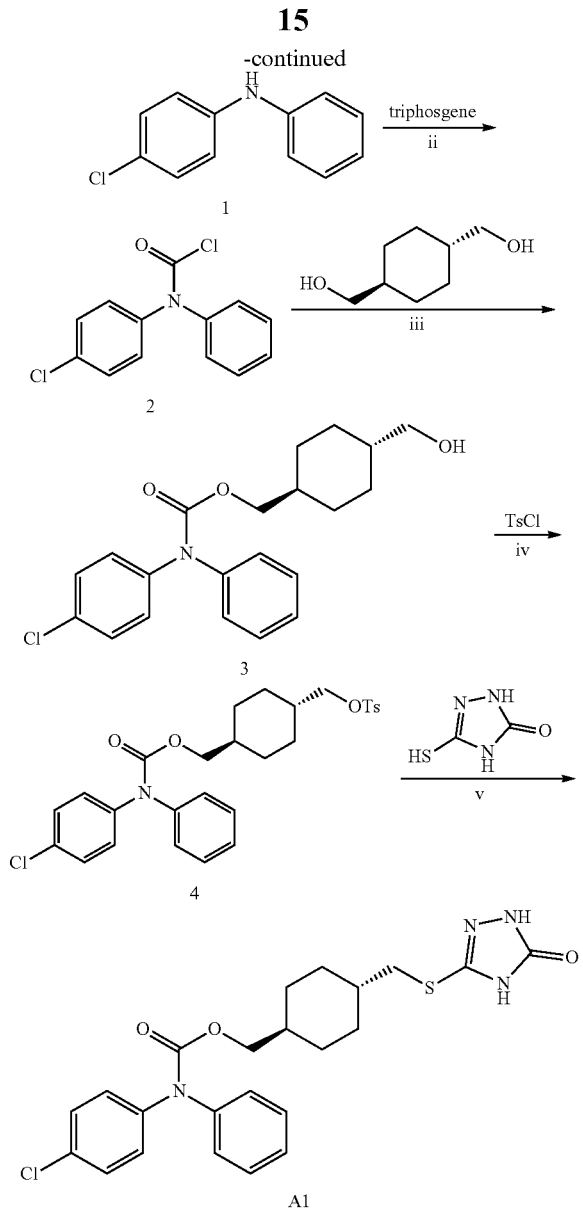

Reagents and conditions. (i) Cu(OAc)$_2$, DBU, DMSO, 120° C., overnight (35%);
(ii) pyridine, DCM, 0° C.~RT, 2 h (92%); (iii) pyridine, reflux, overnight (57%);
(iv) pyridine, DCM, 0° C.~RT, overnight (86%); (v) NaH, DMF, RT, overnight (72%).

Scheme 1. Reagents and conditions. (i) Cu(OAc)$_2$, DMSO, 120° C., overnight (35%); (ii) pyridine, DCM, 0° C.~RT, 2 h (92%); (iii) pyridine, reflux, overnight (57%); (iv) pyridine, DCM, 0° C.~RT, overnight (86%); (v) NaH, DMF, RT, overnight (72%).

4-Chloro-N-phenylaniline (1). To a solution of 4-chloroaniline (0.32 g, 2.5 mmol) and phenylboronic acid (0.46 g, 3.75 mmol) in dry DMSO (5 mL) were added DBU (0.75 mL, 5 mmol) and Cu(OAc)$_2$ (0.91 g, 5 mmol). The resulting dark blue mixture was heated up to 120° C. and stirred overnight. After cooling, the reaction mixture was diluted with EtOAc (100 mL) and then passed through Celite followed by rinsing with EtOAc. The filtrate was washed by brine three times, dried over MgSO$_4$ and concentrated. The residue was purified by column chromatography eluting with 2-5% EtOAc/hxn to yield 0.18 g (35%) of the title compound. $^1$H NMR (400 MHz, Acetone-d$_6$) δ 7.54 (s, 1H), 7.25 (dd, J=15.6, 8.2 Hz, 4H), 7.16-7.08 (m, 4H), 6.90 (t, J=7.3 Hz, 1H).

(4-Chlorophenyl)(phenyl)carbamic chloride (2). To a solution of 4-chloro-N-phenylaniline 1 (0.2 g, 0.98 mmol) in dry DCM (3 mL) at 0° C. was added triphosgene (0.32 g, 1.08 mmol). Pyridine (0.11 mL, 1.38 mmol) predissolved in 1 mL of DCM was added slowly to the reaction mixture. The reaction was stirred for another 15 min and then warmed to RT and stirred for 2 h. It was quenched under cooling by the slow addition of water (the solution turned pink). The mixture was extracted and the aqueous layer was washed again with DCM. The combined organic extracts were washed with brine, dried over MgSO$_4$, concentrated to give 0.24 g (92%) of the title compound as a peach colored solid. This was used in the next step without further purification. $^1$H NMR (400 MHz, Chloroform-d) δ 7.47-7.27 (m, 9H).

((1r,4r)-4-(Hydroxymethyl)cyclohexyl)methyl (4-chlorophenyl)(phenyl)carbamate (3). The carbamic chloride 2 (0.2 g, 0.75 mmol) and (1r,4r)-cyclohexane-1,4-diyldimethanol (0.12 g, 0.83 mmol) were dissolved in pyridine (0.81 mL) in a sealed tube. The reaction mixture was heated overnight under reflux. After cooling, the mixture was partitioned between 1 M HCl and EtOAc. The aq. layer was extracted with EtOAc and the combined organic extracts were washed with brine, dried over MgSO$_4$, and concentrated. The crude was purified via column chromatography eluting with 2-5% MeOH/DCM to yield 0.16 g (57%) of the title compound as a light peach colored solid. $^1$H NMR (400 MHz, Chloroform-d) δ 7.33 (t, J=7.6 Hz, 2H), 7.30-7.26 (m, 2H), 7.24-7.14 (m, 5H), 3.97 (d, J=6.2 Hz, 2H), 3.43 (t, J=5.7 Hz, 2H), 1.78 (d, J=7.9 Hz, 2H), 1.67 (d, J=7.7 Hz, 2H), 1.36 (d, J=11.7 Hz, 1H), 1.23 (t, J=5.8 Hz, 1H), 0.93 (q, J=11.4, 10.5 Hz, 4H).

((1r,4r)-4-((((4-Chlorophenyl)(phenyl)carbamoyl)oxy)methyl)cyclohexyl)methyl 4-methylbenzenesulfonate (4). To an ice cooled solution of alcohol 3 (0.24 g, 0.64 mmol) in dry CH$_2$Cl$_2$ (1.7 mL) was added pyridine (0.41 mL, 5.1 mmol) and TsCl (0.40 g, 2.1 mmol). The reaction mixture was stirred overnight at RT and then washed with 1 N HCl. The aq. phase was extracted with DCM and EtOAc. The organic extracts were washed with brine, dried (MgSO$_4$), and concentrated. The crude was purified via chromatography eluting with 10-20% EtOAc/hxn to yield 0.29 g (86%) of the title compound as a white solid. $^1$H NMR (400 MHz, Chloroform-d) δ 7.77 (d, J=8.1 Hz, 2H), 7.37-7.30 (m, 4H), 7.28 (d, J=2.1 Hz, 2H), 7.25-7.13 (m, 5H), 3.95 (d, J=6.2 Hz, 2H), 3.80 (d, J=6.3 Hz, 2H), 2.45 (s, 3H), 1.68 (d, J=22.0 Hz, 4H), 1.54-1.43 (brs, 2H), 0.87 (d, J=11.7 Hz, 4H).

((1r,4r)-4-(((5-oxo-4,5-dihydro-1H-1,2,4-triazol-3-yl)thio)methyl)cyclohexyl)methyl (4-chlorophenyl)(phenyl)carbamate (A1). To a solution of 5-mercapto-2,4-dihydro-3H-1,2,4-triazol-3-one (47 mg, 0.40 mmol) in DMF (2 mL) was added sodium hydride (60% dispersion in mineral oil, 21 mg, 0.53 mmol). After 15 min, a solution of tosylate 4 (0.14 g, 0.27 mmol) in DMF (3.2 mL) was added dropwise. The reaction mixture was stirred overnight at RT and then quenched with 1 N HCl under cooling. The resulting suspension was extracted with DCM (2×) and EtOAc (2×). The organic extracts were washed with brine, dried over MgSO$_4$, filtered and concentrated. The crude was purified by chromatography eluting with 2-4% MeOH/DCM to provide 0.09 g (72%) of the title compound as a white solid. $^1$H NMR (500 MHz, DMSO-d$_6$) δ 11.60 (brs, 1H), 11.46 (s, 1H), 7.43-7.32 (m, 4H), 7.30-7.21 (m, 5H), 3.86 (d, J=6.1 Hz, 2H), 2.82 (d, J=6.7 Hz, 2H), 1.75 (d, J=11.8 Hz, 2H), 1.55 (d, J=11.7 Hz, 2H), 1.43 (brs, 1H), 1.33 (brs, 1H), 0.85 (dp, J=24.5, 12.2 Hz, 4H). HRMS (ESI): m/z calculated for $C_{23}H_{26}ClN_4O_3S$ [M+H]$^+$ 473.1414, found 473.1411.

Synthesis of ((1s,4s)-4-(2-((5-oxo-4,5-dihydro-1H-1,2,4-triazol-3-yl)thio)ethyl)cyclohexyl)methyl (4-chlorophenyl)(phenyl)carbamate (A2)

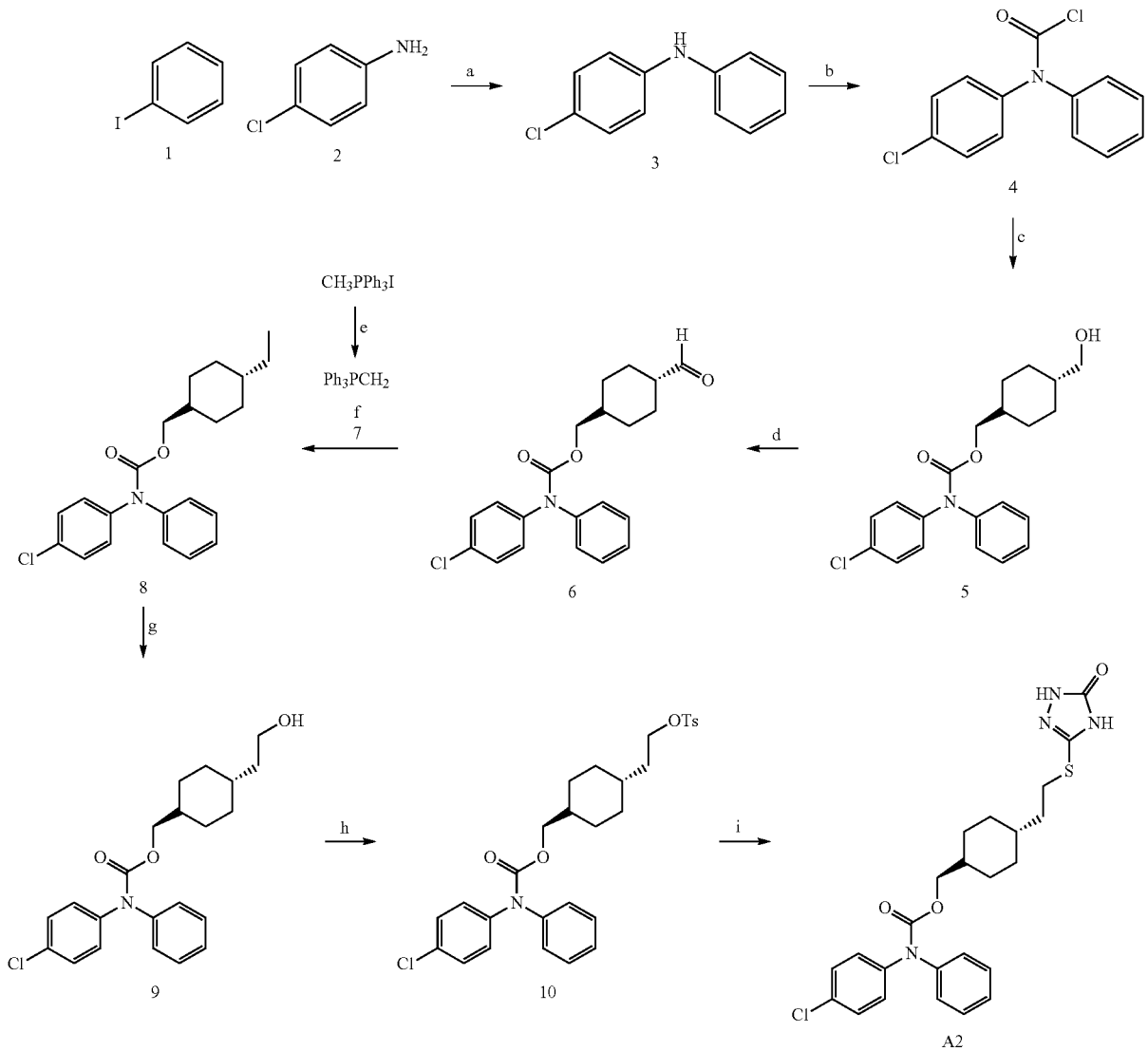

Scheme 1. Reagents and conditions: (a) $K_2CO_3$, CuI, glycerol, 100° C., 16 hrs; (b) triphosgene, pyridine, DCM, 0-23° C., 16 hrs; (c) ((1r,4r)-cyclohexane-1,4-diyl)dimenthanol, pyridine, 120° C., 18 hrs; (d) DMP, DCM, −78-23° C., 3 hrs; (e) KOC(CH$_3$)$_3$, THF, 23° C., 4 hrs; (f) THF, 23° C., 16 hrs; (g) BH$_3$THF, NaOH, H$_2$O$_2$, H$_2$O, THF, 0-23° C., 20 hrs; (h) TsCl, DMAP, DCM, 23° C., 4 hrs; (i) 5-mercapto-2,4-dihydro-3H-1,2,4-triazol-3-one, NaH, DMF, 0-23° C., 4 hrs.

4-chloro-N-phenylaniline (3). To a mixture of 1-chloro-4-iodobenzene (2.5 g, 10 mmol) and glycerol (54 ml) was added aniline (1.9 ml, 21 mmol), KOH (1.2 g, 21 mmol), and CuI (40 mg, 0.21 mmol). The reaction mixture was stirred at 100° C. for 16 hrs. The reaction mixture was cooled to room temp and diluted with water. The mixture was extracted with EtOAc (×3). The organic layer was washed with brine, dried over Na$_2$SO$_4$, filtered and concentrated. The crude residue was purified with column chromatography eluting with DCM. The fractions of desired product were combined, concentrated, and dried under reduced pressure (950 mg, 44%). 1H NMR (400 MHz, Chloroform-d) δ 7.36-7.19 (m, 4H), 7.11-6.94 (m, 5H), 5.67 (s, 1H). 13C NMR (101 MHz, Chloroform-d) δ 142.64, 141.85, 129.68, 129.51, 129.27, 129.07, 125.48, 121.67, 118.98, 118.66, 118.29, 117.93.

(4-chlorophenyl)(phenyl)carbamic chloride (4). To a solution of triphosgene (400 mg, 1.35 mmol) and dry DCM (13 ml) in 0° C. ice bath was added 4-chloro-N-phenylaniline and pyridine (0.65 ml, 8.09 mmol). The reaction was stirred at ambient temperature for 16 hrs. The reaction mixture was quenched with sat NH$_4$Cl and extracted with DCM (×3). The organic layer was washed with 1N HCl, dried over Na$_2$SO$_4$, filtered and concentrated. The crude residue was purified with column chromatography eluting with DCM. The fractions of desired product were combined, concentrated and dried under reduced pressure to obtain the compound (0.9 g, 83%). 1H NMR (400 MHz, Chloroform-d) δ 7.44-7.26 (m, 9H).

((1s,4s)-4-(hydroxymethyl)cyclohexyl)methyl (4-chlorophenyl)(phenyl)carbamate (5). To a solution of (4-chlorophenyl)(phenyl)carbamic chloride (1.1 g, 4.13 mmol) and pyridine (4.4 ml, 55.06 mmol) was added ((1r,4r)-cyclohexane-1,4-diyl)dimethanol (1.19 g, 8.27 mmol). The reaction mixture was stirred at 120° C. under reflux for 18 hrs. The reaction mixture was cooled to room temp and concentrated. The concentrate was resuspended in 1:1 EtO$_2$/EtOAc. The solids were filtered and washed with 1:1 Et$_2$O/EtOAc. The filtrate was concentrated and purified through column chromatography eluting with 1% MeOH in DCM. The fractions of desired product were combined, concentrated and dried under reduced pressure to afford a yellow oil. (1.2 g, 78%). 1H NMR (400 MHz, DMSO-d6) δ 7.44-7.32 (m, 4H), 7.32-7.20 (m, 5H), 4.33 (t, J=5.3 Hz, 1H), 3.88 (d, J=6.1 Hz, 2H), 3.16 (dd, J=5.4, 2.5 Hz, 3H), 1.67 (d, J=10.4 Hz, 2H), 1.55 (t, J=6.1 Hz, 2H), 1.23-1.14 (m, 1H), 0.80 (q, J=11.8 Hz, 4H). MS (ESI), m/z (%): 374 (M$^+$, 100%).

((1s,4s)-4-formylcyclohexyl)methyl (4-chlorophenyl)(phenyl)carbamate (6). To a solution of ((1s,4s)-4-(hydroxymethyl)cyclohexyl)methyl (4-chlorophenyl)(phenyl)carbamate (610 mg, 1.63 mmol) and DCM (5 ml) in −78° C. acetone/dry ice bath was slowly added a solution of DMP (1.04 g, 2.45 mmol) in DCM (20 ml). The reaction mixture was stirred at ambient temperature for 3 hrs. The reaction mixture was quenched with 1:1 sat. NaHCO$_3$/Na$_2$S$_2$O$_3$ (100 ml) and extracted with DCM (×3) The extracts were combined, washed with brine, dried over Na$_2$SO$_4$, filtered, concentrated and dried under reduced pressure. The compound was isolated as white residue (370 mg, 61%). 1H NMR (400 MHz, Chloroform-d) δ 9.57 (s, 1H), 7.48-6.97 (m, 9H), 3.98 (d, J=6.2 Hz, 2H), 2.08 (ddd, J=18.4, 11.1, 5.0 Hz, 1H), 2.01-1.88 (m, 2H), 1.84-1.69 (m, 2H), 1.63-1.51 (m, 1H), 1.20 (qd, J=13.0, 3.6 Hz, 2H), 0.94 (qd, J=12.9, 3.4 Hz, 2H). 13C NMR (101 MHz, Chloroform-d) δ 204.35, 154.53, 142.03, 141.12, 131.39, 129.26, 129.16, 128.81, 128.70, 128.02, 127.58, 127.27, 126.81, 126.30, 70.72, 50.08, 36.60, 28.29, 28.13, 25.33, 25.13. MS (ESI), m/z (%): 372 (M$^+$, 100%).

((1s,4s)-4-vinylcyclohexyl)methyl (4-chlorophenyl)(phenyl)carbamate (8), To the mixture of methyltriphenylphosphonium iodide (750 mg, 1.85 mmol) and THF (5.4 ml) was added potassium tert-butoxide (218 mg, 1.94 mmol). The reaction mixture was stirred at ambient temperature for 4 hrs to obtain the Wittig reagent in THF. The mixture was added to a solution of ((1s,4s)-4-formylcyclohexyl)methyl (4-chlorophenyl)(phenyl)carbamate (0.37 g, 0.99 mmol) and THF (1 ml). The reaction mixture was stirred at ambient temperature for 16 hrs and quenched with water. The mixture was extracted with DCM (×3). The organic layer was washed with water, brine, dried over Na$_2$SO$_4$, filtered and concentrated. The crude residue was purified with column chromatography eluting with 75-100% DCM in hexane. The fractions of the desired product were combined, concentrated, and dried under reduced pressure (0.21 g, 56%). 1H NMR (400 MHz, Chloroform-d) δ 7.42-7.09 (m, 9H), 5.75 (ddd, J=17.1, 10.4, 6.4 Hz, 1H), 5.03-4.80 (m, 2H), 3.98 (d, J=6.3 Hz, 2H), 1.83 (d, J=9.7 Hz, 1H), 1.80-1.71 (m, 2H), 1.71-1.62 (m, 2H), 1.53-1.47 (m, 1H), 1.13-0.91 (m, 4H).

((1s,4s)-4-(2-hydroxyethyl)cyclohexyl)methyl (4-chlorophenyl)(phenyl)carbamate (9). To a solution of ((1s,4s)-4-vinylcyclohexyl)methyl (4-chlorophenyl)(phenyl)carbamate (227 mg, 0.61 mmol) and THF (2 ml) in 0° C. ice bath was added BH$_3$-THF (0.3 ml, 0.3 mmol). The reaction mixture was stirred at ambient temperature for 8 hrs. Water (0.01 ml, 0.6 mmol), 3N NaOH (0.2 ml, 0.61 mmol), and H$_2$O$_2$ (0.2 ml, 0.61 mmol) were added slowly into the mixture in the 0° C. ice bath. The reaction mixture was stirred at ambient temperature for 14 hrs. The mixture was quenched with sat NaHSO$_3$ and extracted with DCM (×3). The organic layer was washed with brine, dried over Na$_2$SO$_4$, filtered, concentrated and dried under reduced pressure. The compound was isolated as clear oil (183 mg, 77%). 1H NMR (400 MHz, Chloroform-d) δ 7.41-7.08 (m, 9H), 3.96 (d, J=6.4 Hz, 2H), 3.63 (t, J=6.8 Hz, 2H), 1.76-1.60 (m, 4H), 1.53 (dtt, J=11.4, 7.1, 4.0 Hz, 1H), 1.43 (q, J=6.8 Hz, 2H), 1.34-1.26 (m, 1H), 0.91 (qd, J=11.7, 10.0, 2.6 Hz, 4H).

2-((1s,4s)-4-((((4-chlorophenyl)(phenyl)carbamoyl)oxy)methyl)cyclohexyl)ethyl 4-methylbenzenesulfonate (10). To a solution of ((1s,4s)-4-(2-hydroxyethyl)cyclohexyl)methyl (4-chlorophenyl)(phenyl)carbamate (9) (137 mg, 0.35 mmol) and DCM (5 ml) was added DMAP (86.3 mg, 0.71 mmol) and 4-methylbenzenesulfonyl chloride (135 mg, 0.71 mmol). The reaction mixture was stirred at ambient temperature for 4 hrs. The mixture was quenched with water and was extracted with DCM (×3). The organic layer was washed with brine, dried over Na$_2$SO$_4$, filtered and concentrated. The crude residue was purified through column chromatography eluting with 5% MeOH in DCM. The fractions of desired product were combined, concentrated, and dried under reduced pressure. The compound was isolated as colorless oil (130 mg, 68%). 1H NMR (400 MHz, DMSO-d6) δ 7.86-7.65 (m, 2H), 7.55-7.17 (m, 11H), 4.00 (t, J=6.3 Hz, 2H), 3.84 (d, J=6.2 Hz, 2H), 2.39 (s, 3H), 1.57-1.29 (m, 7H), 1.08 (d, J=6.2 Hz, 1H), 0.83-0.63 (m, 4H). 13C NMR (101 MHz, Chloroform-d) δ 154.58, 144.70, 142.11, 141.20, 133.07, 131.33, 129.84, 129.78, 129.01, 128.99, 128.93, 128.91, 127.89, 127.85, 127.77, 127.05, 127.04, 126.47, 71.13, 68.59, 37.06, 35.85, 33.63, 31.88, 29.07, 21.68.

((1s,4s)-4-(2-((5-Oxo-4,5-dihydro-1H-1,2,4-triazol-3-yl)thio)ethyl)cyclohexyl)methyl (4-chlorophenyl)(phenyl)carbamate (A2). To a solution of 5-mercapto-2,4-dihydro-3H-1,2,4-triazol-3-one (39 mg, 0.33 mmol) and DMF (1 ml) in 0° C. ice bath was added NaH (18 mg, 0.44 mmol). The mixture was stirred at ambient temperature for 20 min. 2-((1s,4s)-4-((((4-Chlorophenyl)(phenyl)carbamoyl)oxy)methyl)cyclohexyl)ethyl 4-methylbenzenesulfonate (0.12 g, 0.22 mmol) was dissolved in DMF (5 ml) and added into the mixture. The mixture was stirred at ambient temperature for 4 hrs, quenched with ice water and extracted with EtOAc (×3). The aqueous layer was neutralized with 2N HCl until the pH was 7 and extracted with EtOAc (×2). The organic layer was washed with brine, dried over Na$_2$SO$_4$, filtered, and concentrated. The crude residue was purified with column chromatography eluting with 2% MeOH in DCM. The fractions of desired product were combined, concentrated and dried under reduced pressure. The compound was isolated as a white solid (90 mg, 83%). 1H NMR (400 MHz, DMSO-d6) δ 11.63 (s, 1H), 11.48 (s, 1H), 7.45-7.32 (m, 4H), 7.31-7.20 (m, 5H), 3.86 (d, J=6.2 Hz, 2H), 3.00-2.86 (m, 2H), 1.65 (d, J=8.3 Hz, 2H), 1.54 (d, J=8.3 Hz, 2H), 1.43 (q, J=7.2 Hz, 3H), 1.20 (d, J=12.5 Hz, 1H), 0.91-0.71 (m, 4H). 13C NMR (101 MHz, DMSO-d6) δ 156.61, 154.27, 142.45, 141.85, 141.84, 129.50, 129.29, 129.01, 128.97, 127.72, 127.00, 70.89, 37.19, 36.96, 36.46, 31.86, 29.12, 29.06. MS (ESI), m/z (%): 487 (M+, 100%).

Synthesis of 5-((4-((5,6-diphenylpyrazin-2-yl)(isopropyl)amino)butyl)thio)-2,4-dihydro-3H-1,2,4-triazol-3-one (A3)

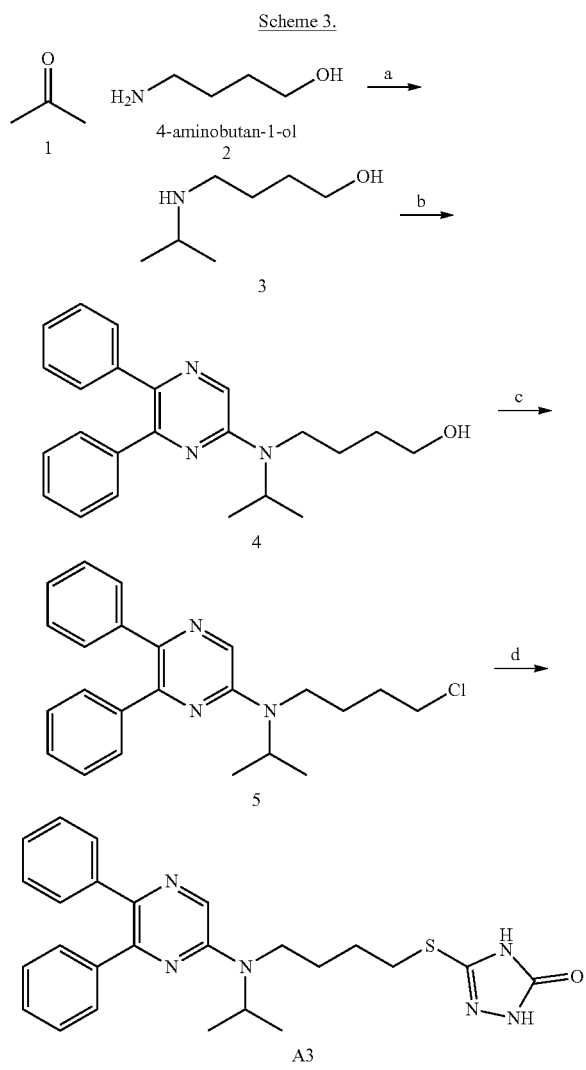

Reagents and conditions: (a) Platinum(IV) oxide, EtOH, ambient temp, 7 days; (b) 5-bromo-2,3-diphenylpyrazine, KI, 140° C., 2 days; (c) DMAP, 4-methylbenzenesulfonyl chloride, DCM, ambient temp, 18 hrs; (d) 5-mercapto-2,4-dihydro-3H-1,2,4-triazol-3-one, NaH, DMF, ambient temp, 2 days.

Scheme 3. Reagents and conditions: (a) Platinum(IV) oxide, EtOH, ambient temp, 7 days; (b) 5-bromo-2,3-diphenylpyrazine, KI, 140° C., 2 days; (c) DMAP, 4-methylbenzenesulfonyl chloride, DCM, ambient temp, 18 hrs; (d) 5-mercapto-2,4-dihydro-3H-1,2,4-triazol-3-one, NaH, DMF, ambient temp, 2 days.

4-(isopropylamino)butan-1-ol (3). To a solution of 4-aminobutan-1-ol (2.7 ml, 29 mmol) in acetone (3.5 ml, 47 mmol) was added platinum(IV) oxide (67 mg, 0.29 mmol). The mixture stirred under $H_2$ atmosphere at ambient temperature for 7 days. The reaction mixture was filtered through Celite, and concentrated under reduced pressure to afford a colorless oil (3.72 g 97%). 1H NMR (400 MHz, Chloroform-d) δ 3.43 (t, J=5.3 Hz, 2H), 2.67 (hept, J=6.3 Hz, 1H), 2.50 (t, J=5.7 Hz, 2H), 1.49 (ddt, J=13.2, 7.8, 4.7 Hz, 4H), 0.95 (d, J=6.5 Hz, 6H). 13C NMR (101 MHz, Chloroform-d) δ 62.11, 48.55, 46.92, 32.23, 28.80, 22.52.

4-((5,6-diphenylpyrazin-2-yl)(isopropyl)amino)butan-1-ol (4). To a mixture of 5-bromo-2,3-diphenylpyrazine (1 g, 3.21 mmol) and 4-(isopropylamino)butan-1-ol (2.32 g, 17.7 mmol) was added potassium iodide (266 mg, 1.6 mmol). The mixture was stirred in a pressure vessel at 140° C. for 2 days. The reaction mixture was cooled to room temp and diluted with water. The mixture was extracted with EtOAc (×4) and the combined organic layers washed with brine, dried over $Na_2SO_4$, filtered and concentrated. The crude residue was purified with column chromatography eluting with 0-2% MeOH in DCM. The fractions of the desired product were combined, concentrated, and dried under reduced pressure to obtain a brown oil (0.82 g, 71%). 1H NMR (400 MHz, Chloroform-d) δ 8.02 (s, 1H), 7.49-7.42 (m, 2H), 7.39-7.33 (m, 2H), 7.29-7.21 (m, 6H), 4.78 (p, J=6.7 Hz, 1H), 3.68 (t, J=6.4 Hz, 2H), 3.43 (dd, J=9.2, 6.7 Hz, 2H), 1.76 (qd, J=7.8, 7.1, 3.9 Hz, 2H), 1.65 (q, J=6.8 Hz, 2H), 1.28 (d, J=6.7 Hz, 6H).

N-(4-chlorobutyl)-N-isopropyl-5,6-diphenylpyrazin-2-amine (5). To a solution of 4-((5,6-diphenylpyrazin-2-yl)(isopropyl)amino)butan-1-ol (200 mg, 0.55 mmol) and dry DCM (8 ml) was added 4-methylbenzenesulfonyl chloride (320 mg, 1.68 mmol) and DMAP (210 mg, 1.72 mmol). The reaction was stirred at ambient temperature for 18 hrs. The reaction mixture was diluted with water and extracted with DCM (×3). The organic layer was washed with brine, dried over $Na_2SO_4$, filtered and concentrated. The crude residue was purified with column chromatography eluting with DCM. The fractions of desired product were combined, concentrated, and dried under reduced pressure. The compound was isolated as a white solid (170 mg, 81%). 1H NMR (400 MHz, Chloroform-d) δ 8.02 (s, 1H), 7.49-7.43 (m, 2H), 7.37 (dt, J=7.6, 1.4 Hz, 2H), 7.29-7.22 (m, 6H), 4.75 (p, J=6.7 Hz, 1H), 3.60 (t, J=6.0 Hz, 2H), 3.45 (t, J=7.3 Hz, 2H), 1.87 (dt, J=8.5, 3.5 Hz, 4H), 1.29 (d, J=6.7 Hz, 6H). MS (ESI), m/z (%): 380 (M+, 100%).

5-((4-((5,6-diphenylpyrazin-2-yl)(isopropyl)amino) butyl)thio)-2,4-dihydro-3H-1,2,4-triazol-3-one (A3). To a solution of 5-mercapto-2,4-dihydro-3H-1,2,4-triazol-3-one (92.5 mg, 0.79 mmol) and DMF (2 ml) in 0° C. ice bath was added NaH (55 mg, 1.38 mmol). N-(4-chlorobutyl)-N-isopropyl-5,6-diphenylpyrazin-2-amine (150 mg, 0.4 mmol) was dissolved in DMF (9 ml) and added to the mixture. The reaction was stirred at ambient temperature for 2 days. The reaction mixture was quenched with ice water and extracted with EtOAc (×3). The pH of the aqueous layer was adjusted to 7 with 2N HCl, followed by extraction with EtOAc (×2). The organic layer was washed with brine, dried over $Na_2SO_4$, filtered and concentrated. The crude residue was purified with column chromatography eluting 2% MeOH in DCM. The fractions of the desired product were combined, concentrated and dried under reduced pressure to obtain a white solid (109 mg, 60%). 1H NMR (400 MHz, DMSO-d6) δ 11.67 (s, 1H), 11.52 (s, 1H), 8.12 (s, 1H), 7.44-7.04 (m, 10H), 4.86-4.59 (m, 1H), 3.39 (d, J=7.2 Hz, 2H), 3.09-2.96 (m, 2H), 1.70 (q, J=4.0, 3.5 Hz, 4H), 1.20 (d, J=6.7 Hz, 6H). 13C NMR (101 MHz, DMSO-d6) δ 156.63, 151.57, 151.57, 148.51, 141.79, 139.86, 139.72, 138.55, 138.55, 130.01, 129.73, 129.66, 129.39, 128.57, 128.42, 128.19, 127.95, 46.15, 31.17, 28.15, 27.19, 20.47, 20.32. MS (ESI), m/z (%): 461 (M+, 100%).

Pharmacokinetic Study of the the Inhibitors in Mice Blood Plasma

The blood plasma concentration of compound A3 in mice was determined following per os, oral compound administration ("PO") and intravenous ("IV") administration Specificity. The chromatograms of blank plasma and the blank plasma/spiked with internal standard (CE302) showed that the blank plasma has no significant interference to compound A3 and IS determination.

Calibration curve. The concentration range was evaluated from 1-5000 ng/ml for compound A3. The curve was built with linear regression with weighing (1/X2). The linear regression analysis was performed by plotting the peak area ratio (y) against the concentration (x) in ng/mL. The linearity of the relationship between peak area ratio and concentration was demonstrated by the correlation coefficients (R) obtained for the linear regression.

Instrument Conditions. The LC-MS and mass spectrometry conditions for the compounds tested are shown below.

| Chromatographic Conditions: | |
|---|---|
| Column: | 5 cm × 2.1 mm I.D., packed with 1.7 μm Aquity BEH C18 (Waters) |
| Mobile Phase A: | 0.1% formic acid in purified deionized water |
| Mobile Phase B: | 0.1% formic acid in acetonitrile |
| Flow Rate: | 0.4 mL/min |
| Injection Volume: | 5 μL |
| Run Time: | 4.5 min |

| Gradient Program: | | |
|---|---|---|
| Time | % A | % B |
| 0.01 | 95 | 5 |
| 0.30 | 95 | 5 |
| 0.80 | 1 | 99 |
| 2.50 | 1 | 99 |
| 2.51 | 95 | 5 |
| 4.50 | 95 | 5 |

| Mass Spectrometry Conditions: | | | | | | |
|---|---|---|---|---|---|---|
| Compound | Formula/ Mass | Precursor ion (m/z) | Product ion (m/z) | Dwell (secs) | Cone Voltage | Col. Energy |
| A2 | 452 | 452.941 | 136.96 | 0.01 | 20 | 16 |
| A3 | 492 | 492.974 | 136.959 | 0.01 | 26 | 18 |
| A1 | 418 | 416.916 | 281.045 | 0.01 | 38 | 14 |
| CE302 | 454 | 455.16 | 425.2 | 0.01 | 76 | 31 |

Results. The individual and average compound A3 concentration-time data for IV and PO dosed groups are listed in Table 1, and graphically presented in FIG. 1.

TABLE 1

Compound A3 Concentration in Mouse Plasma following PO and IV administration at 2, 4, and 7 hours.

| | | Compound A3 Concentration in Plasma (ng/ml) | | | | |
|---|---|---|---|---|---|---|
| | Time point (h) | Mouse 1 | Mouse 2 | Mouse 3 | Mean | SD |
| IV (30 mg/kg) | 2 | 203.3 | 157.9 | 130.6 | 163.9 | 36.7 |
| | 4 | 135.1 | 80.3 | 101.9 | 105.8 | 27.6 |
| | 7 | 123.3 | 76.9 | 92.7 | 97.6 | 23.6 |
| PO (30 mg/kg) | 2 | 186.3 | *809.0 | 52.5 | 119.4 | 94.6 |
| | 4 | 46.5 | *812.7 | 22.5 | 34.5 | 17.0 |
| | 7 | 46.3 | 19.1 | 19.3 | 28.3 | 15.6 |

*outliers

Preparation of Washed Human Platelets

Citrated whole blood was centrifuged (200 g for 10 min) to isolate platelet-rich plasma. Platelet-rich plasma was treated with acid citrate dextrose (2.5% sodium citrate, 1.5% citric acid, 2.0% D-glucose) and apyrase (0.02 U/mL), and then centrifuged (2000 g for 10 mins) to pellet the platelets. Platelets were resuspended at $3.0 \times 10^8$ platelets/mL in Tyrode's buffer (10 mM HEPES, 12 mM $NaHCO_3$, 127 mM NaCl, 5 mM KCl, 0.5 mM $NaH_2PO_4$, 1 mM $MgCl_2$, and 5 mM glucose) unless otherwise stated.

Platelet Aggregation

Figure 2:
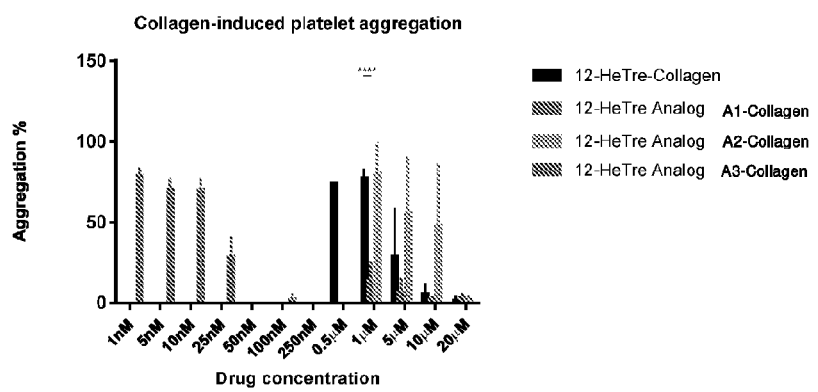
FIG. 2 depicts the percentage of collagen-induced platelet aggregation for compounds A1, A2, and A3 at 1 µM, 5 µM, 10 µM, and 20 µM, as further described in the Examples section.
Figure 3:
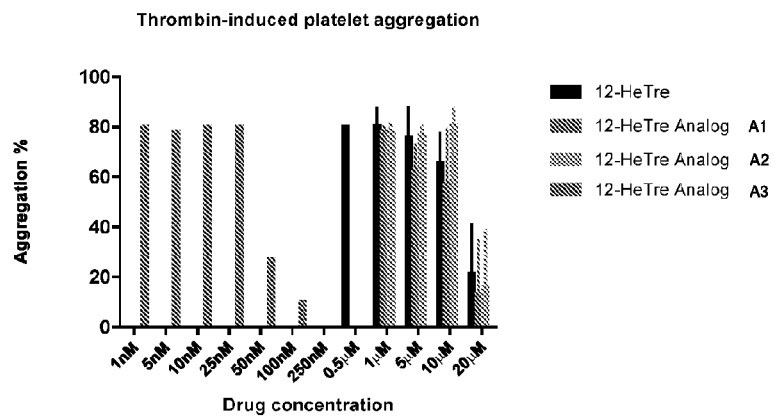
FIG. 3 depicts the percentage of thrombin-induced platelet aggregation for compounds A1, A2, and A3 at 1 µM, 5 µM, 10 µM, and 20 µM, as further described in the Examples section.

Washed human platelets were prepared at $3 \times 10^8$ platelets/ml and aggregation was measured in a 4-channel Lumi-aggregometer (Chonolog Inc, Model 700D) under stirring conditions at 1100 RPM at 37° C. Platelets were incubated with increasing concentrations of Compounds A1, A2, and A3 (1 μM to 20 μM) for 10 minutes and platelet aggregation was induced by an $EC_{80}$ concentration of thrombin or collagen. Each condition was repeated with platelets from 5 independent volunteers (N=5). Inhibition of aggregation was considered statistically significant if there was a significant decrease in aggregation compared to HETre treated conditions. *, $P<0.05$; , $P<0.01$; *, $P<0.001$; ****, $P<0.0001$. See FIG. 2 and FIG. 3.

Vasodilator-Stimulated Phosphoprotein Phosphorylation in Human Platelets

Figure 4:
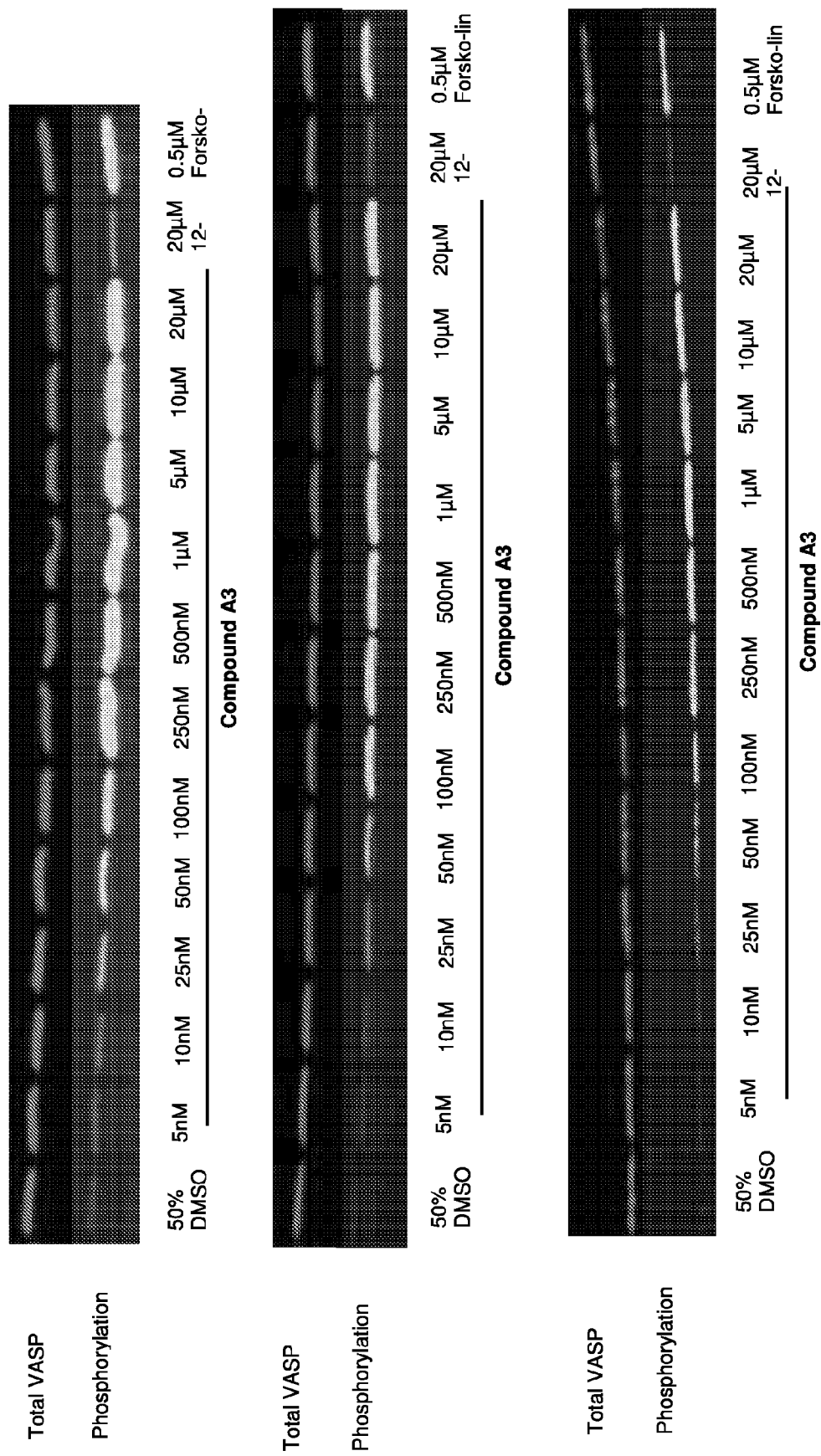
FIG. 4 depicts the total and phospho-VASP (serine 157) with compound A3, quantified by Western Blot using an Odyssey imaging system (LI-CoR).
Figure 5A:
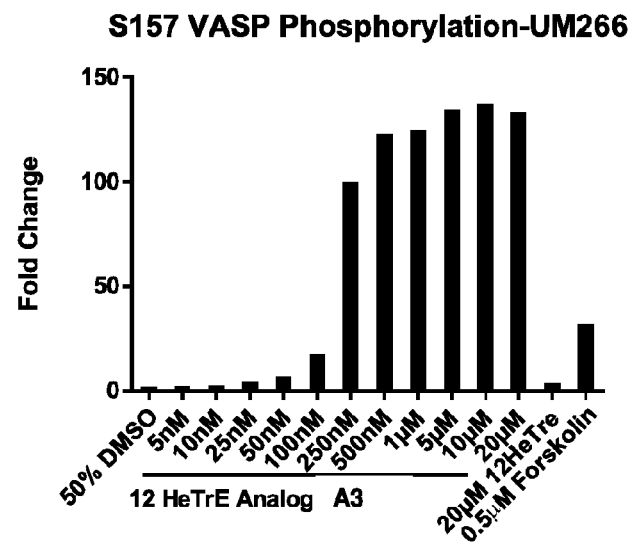
FIG. 5A-5E depicts effect of compound A3 on the fold change at different concentrations during VASP phosphorylation.
Figure 5B:
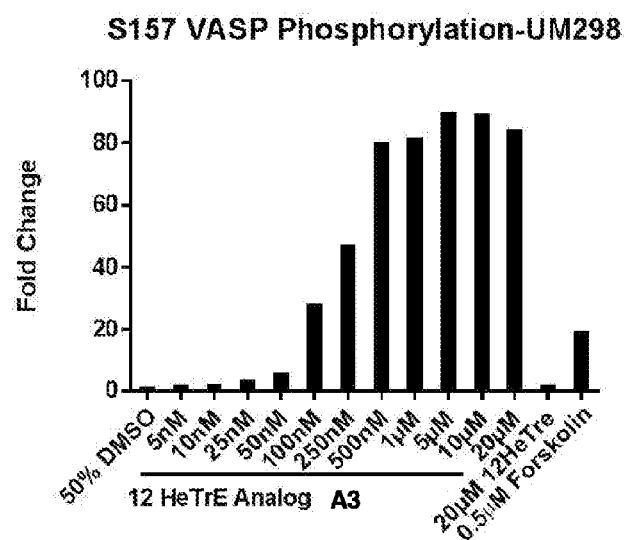
Figure 5C:
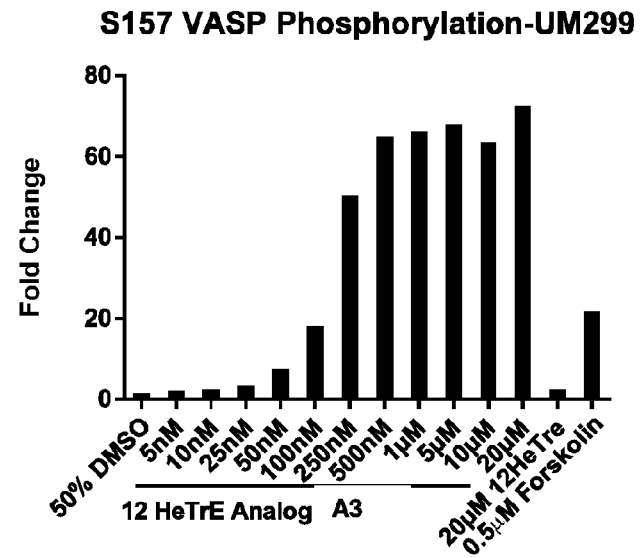
Figure 5D:
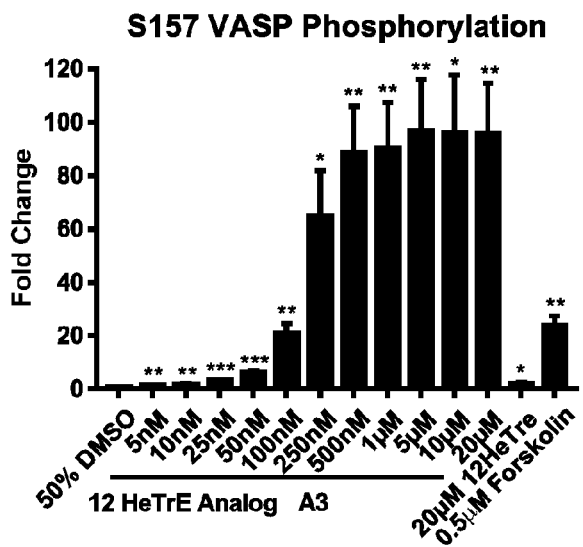
Figure 5E:
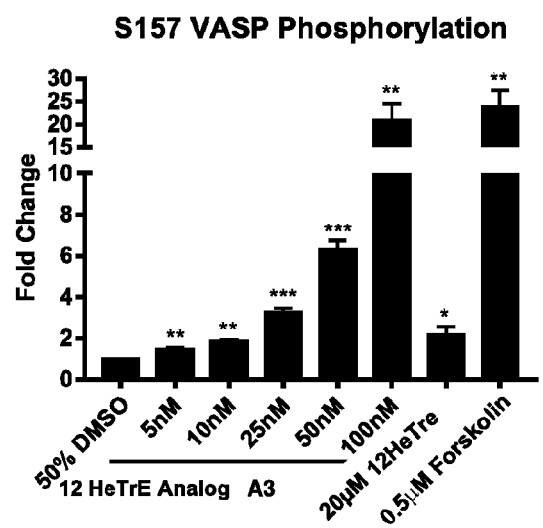

Washed platelets were treated with forskolin (0.5 μM), 12-HETre (20 μM), or compound A3 (5 nm, 10 nm, 25 nm, 50 nm, 100 n, 250 nm, 1 μM, 5 μM, 10 μM, and 20 μM) for one minute, then directly lysed in 5× Laemmli sample buffer (1.5 M Tris-HCl, pH 6.8, glycerol, 5% β-mercaptoethanol, 10% sodium dodecyl sulfate (SDS), and 1% bromophenol blue). The samples were boiled for five minutes and then run on a 10% SDS-PAGE gel. The levels of total and phospho-VASP (serine 157) were quantified by Western Blot using an Odyssey imaging system (LI-CoR). As expected, forskolin treated platelets also had an increase in VASP phosphorylation. Compound A3 induced VASP phosphorylation at a concentration as low as 10 nm. See FIGS. 4 and 5.

In Vivo Pharmacokinetics Following Oral Administration in Mice

Compound A3 was orally administered to mice (30 mg/kg), and the drug concentration of plasma in mice (n=3) was monitored at 8 time points (0.25, 0.5, 1, 2, 4, 8, 12, and 24 hours) and assessed by PK analysis as described, supra.

Compound Pre-Treatments on Experimental Mice for In Vivo Studies

C57BL/6 wild-type (WT) control mice were purchased from Jackson Laboratories (Bar Harbor, ME, USA) and housed in the research facility at the University of Michigan. Compound A1 was synthesized and specifically formulated in Polyethylene Glycol 300 (PEG 300) for oral gavage dosing in mice for in vivo thrombosis and hemostasis studies. For laser-induced cremaster arteriole thrombosis model, mice were treated with compound A1 (3 mg/kg) or with PEG 300 via oral administration 2 times per day for 2 days prior to intravital microscopy studies on the third day.

Laser-Induced Cremaster Arteriole Thrombosis Model

Adult mice (10-12 weeks old) were anesthetized as described above and surgically prepared as described in detail, and a tracheal tube was inserted to facilitate breathing. The cremaster muscle was prepared and perfused with preheated bicarbonate-buffered saline throughout the experiment. DyLight 488-conjugated rat anti-mouse platelet GP1bβ antibody (0.1 µg/g; EMFRET Analytics) and Alexa Fluor 647-conjugated anti-fibrin (0.3 µg/g) or Alexa Flour 647 rat-anti mouse CD62P (3 µg/mouse) were administered by a jugular vein cannula prior to vascular injury. Multiple independent thrombi were induced in the arterioles (30-50 µm diameter) in each mouse by a laser ablation system (Ablate! photoablation system; Intelligent Imaging Innovations, Denver, CO, USA). Images of thrombus formation at the site of injured arterioles were acquired in real-time under 63× water-immersion objective with a Zeiss Axio Examiner Z1 fluorescent microscope equipped with solid laser launch system (LaserStack; Intelligent Imaging Innovations) and high-speed sCMOS camera. All captured images were analyzed for the change of fluorescent intensity over the course of thrombus formation after subtracting fluorescent background defined on an uninjured section of the vessel using the Slidebook program.

Figure 6:
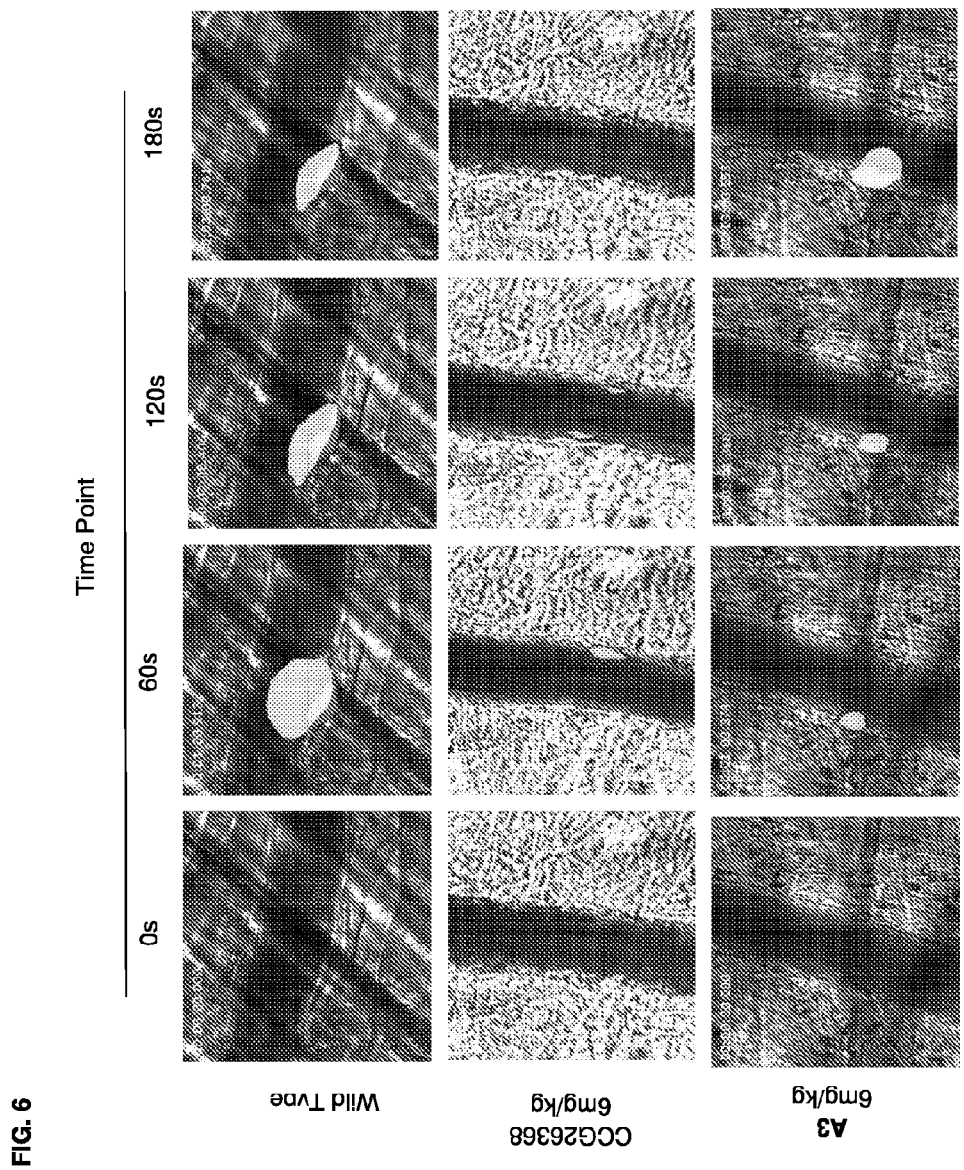
FIG. 6 depicts representative images of platelet accumulation (green) and fibrin formation (red) in growing thrombi in cremaster arterioles in a wild-type ("WT") control animal treated with polyethylene glycol ("PEG"; control, upper), WT treated with compound CCG26368 (6 mg/kg, twice a day for 2 days; middle), and WT treated with compound A3 (6 mg/kg, twice a day for 2 days; lower), as further described in the Examples section.

Representative images of platelet accumulation (green) and fibrin formation (red) in growing thrombi in cremaster arterioles in a wild-type (WT) control animal treated with polyethylene glycol (PEG; control, upper), WT treated with compound CCG26368 (6 mg/kg, twice a day for 2 days; middle), and WT treated with compound A3 (6 mg/kg, twice a day for 2 days; lower) are shown in FIG. 6, demonstrating that compound A3 impairs thrombus formation in laser-induced cremaster arteriole thrombosis models.

Figure 7:
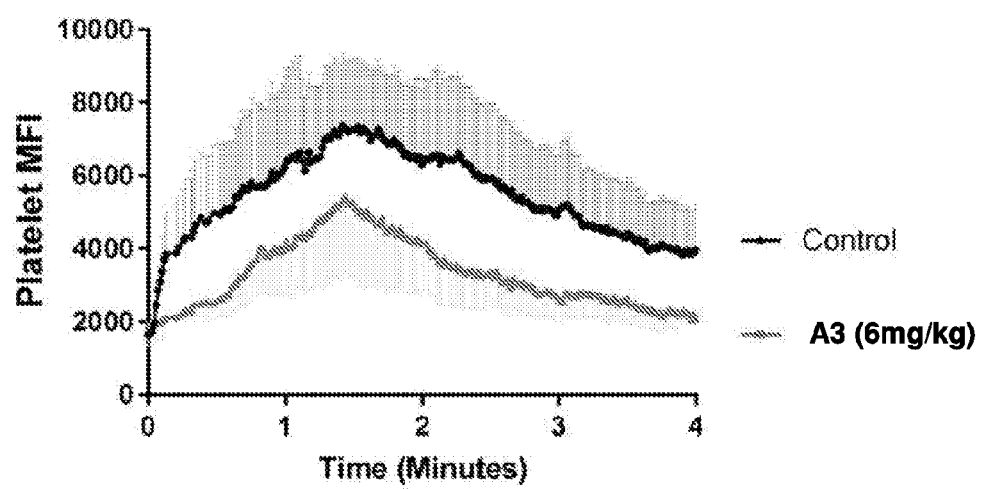
FIG. 7 depicts the mean fluorescence intensity ("MFI") of platelet accumulation at the site of injury were recorded over time in control mice and mice treated with compound A3 (6 mg/kg, twice a day for 2 days), as further described in the Examples section. Data represents mean±SEM; two-way ANOVA.
Figure 8:
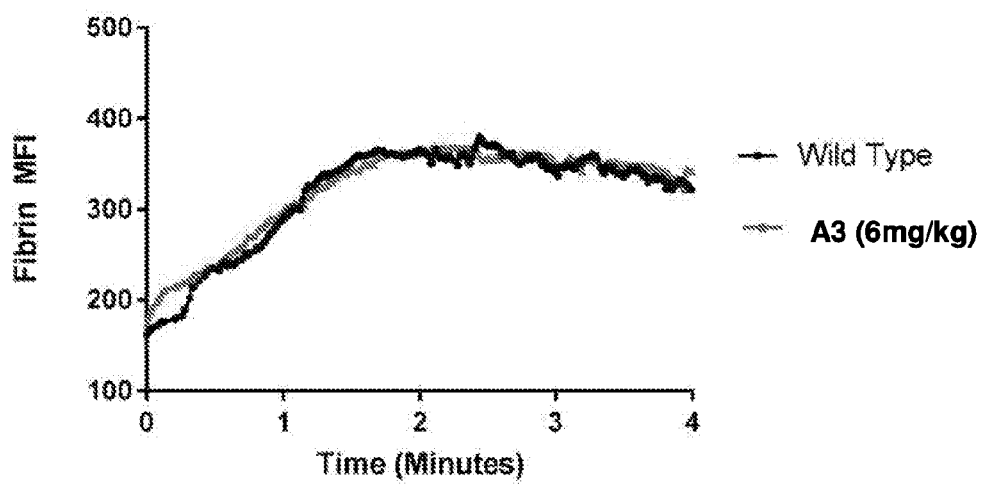
FIG. 8 depicts the mean fluorescence intensity ("MFI") of fibrin accumulation at the site of injury were recorded over time in control mice and mice treated with compound A3 (6 mg/kg, twice a day for 2 days), as further described in the Examples section. Data represents mean±SEM; two-way ANOVA.

Mean fluorescence intensity (MFI) of platelet and fibrin accumulation at the site of injury were recorded over time in control mice and mice treated with compound A3 (6 mg/kg, twice a day for 2 days). Wild-type mice treated with compound A3 were able for reduce thrombus growth (platelet and fibrin accumulation) following laser-induced injury of the arteriole of the cremaster muscle. See FIG. 7 and FIG. 8.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:

1. A compound of Formula (I), or a pharmaceutically acceptable salt thereof:

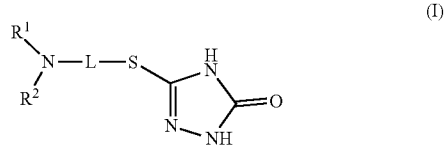

wherein:

each of $R^1$ and $R^2$ independently is $C_{6-10}$aryl optionally substituted with 1-2 groups selected from $C_{1-6}$alkyl, halo, and aryl;

L is $-(CO_2)_s-(CH_2)_m-(Cy)_r-(CH_2)_n-$;

Cy is $C_{3-8}$cycloalkylene;

m is 1 or 2;

n is 1, 2, 3, 4, or 5; and r and s are each independently 0 or 1.

2. The compound or salt of claim 1, wherein each of $R^1$ and $R^2$ independently is $C_{6-10}$aryl.

3. The compound or salt of claim 2, wherein $R^1$ and $R^2$ are each phenyl optionally substituted with 1-2 groups selected from $C_{1-6}$alkyl, halo, and aryl.

4. The compound or salt of claim 3, wherein:

(i) each phenyl is unsubstituted; or (ii) at least one phenyl is substituted with halo.

5. The compound or salt of claim 4, wherein halo is Cl.

6. The compound or salt of claim 1, wherein r and s are each 1.

7. The compound or salt of claim 6, wherein Cy is cyclopentylene or cyclohexylene.

8. The compound or salt of claim 6, wherein m is 1, and/or n is 1 or 2.

9. The compound or salt of claim 1, wherein r and s are each 0.

10. The compound or salt of claim 9, wherein n+m is 3, 4, 5, or 6.

11. A compound or pharmaceutically acceptable salt thereof having a structure

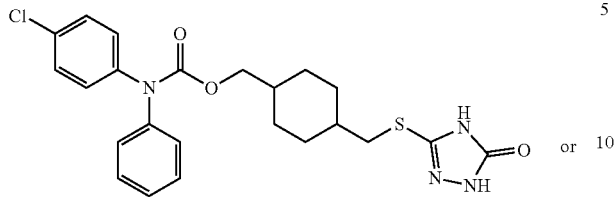 or

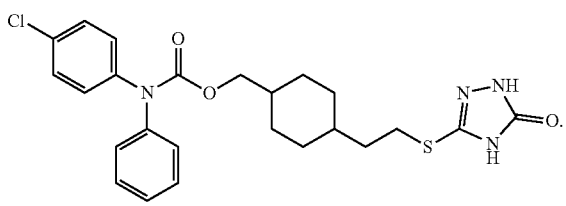

12. The compound or salt of claim 11 having a structure

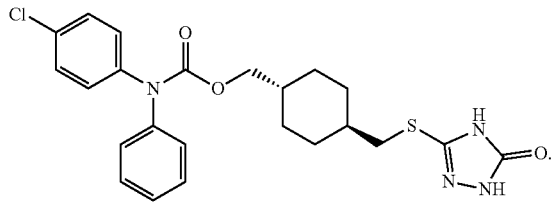 [SMILES: O=C(OC[C@H]1CC[C@H](CSc2n[nH]c(=O)[nH]2)CC1)N(c1ccccc1)c1ccc(Cl)cc1]

13. The compound or salt of claim 11, having a structure of

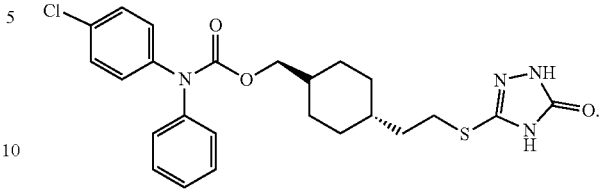

14. A pharmaceutical composition comprising the compound or salt of claim 1 and a pharmaceutically acceptable carrier.

15. A method of inhibiting platelet aggregation or platelet integrin activation in a cell, comprising contacting the cell with the compound of claim 1 in an amount effective to inhibit platelet aggregation or platelet integrin activation.

16. A method of activating one or more of $G\alpha_s$-linked G Protein-coupled receptors ("GPCRs"), cAMP, and protein kinase A ("PKA") in a cell, comprising contacting the cell with the compound of claim 1 in an amount effective to activate GPCRs, cAMP and/or PKA.

17. A method of inhibiting thrombus growth in a subject in need thereof, comprising administering to the subject a therapeutically effective amount of the compound of claim 1.

18. A method of treating a thrombotic disorder or thrombocytopenia in a subject in need thereof comprising administering to the subject a therapeutically effective amount of the compound of claim 1.

19. The method of claim 18, wherein the thrombotic disorder is selected from arterial thrombosis, deep vein thrombosis ("DVT"), pulmonary embolism ("PE"), ischemic stroke, immune thrombocytopenia ("ITP"), Heparin-induced thrombocytopenia ("HIT"), and Heparin-induced thrombocytopenia and thrombosis ("HITT").

20. A method of preventing thrombosis in a subject comprising administering to the subject a therapeutically effective amount of the compound of claim 1.

* * * * *